US012567503B2

(12) United States Patent
Alon et al.

(10) Patent No.: US 12,567,503 B2
(45) Date of Patent: Mar. 3, 2026

(54) SYSTEM TO DETECT DIELECTRIC CHANGES IN MATTER

(71) Applicant: NEW YORK UNIVERSITY, New York, NY (US)

(72) Inventors: Leeor Alon, New York, NY (US); Seena Dehkharghani, Larchmont, NY (US)

(73) Assignee: NEW YORK UNIVERSITY, New York, NY (US)

( * ) Notice: Subject to any disclaimer, the term of this patent is extended or adjusted under 35 U.S.C. 154(b) by 0 days.

(21) Appl. No.: 18/732,389

(22) Filed: Jun. 3, 2024

(65) Prior Publication Data

US 2024/0321456 A1     Sep. 26, 2024

Related U.S. Application Data

(60) Division of application No. 17/370,983, filed on Jul. 8, 2021, now Pat. No. 12,002,584, which is a continuation-in-part of application No. PCT/US2020/013204, filed on Jan. 10, 2020.

(60) Provisional application No. 62/791,669, filed on Jan. 11, 2019.

(51) Int. Cl.
| | |
|---|---|
| *G16H 50/20* | (2018.01) |
| *G06N 3/08* | (2023.01) |
| *G16H 10/60* | (2018.01) |
| *G16H 30/20* | (2018.01) |
| *G16H 40/63* | (2018.01) |

(52) U.S. Cl.
CPC .............. *G16H 50/20* (2018.01); *G06N 3/08* (2013.01); *G16H 10/60* (2018.01); *G16H 30/20* (2018.01); *G16H 40/63* (2018.01)

(58) Field of Classification Search
CPC ........ G16H 50/20; G16H 10/60; G16H 30/20; G16H 40/63; G16H 30/40; G16H 70/60; G06N 3/08; A61B 5/0507; A61B 5/7267
See application file for complete search history.

(56) References Cited

U.S. PATENT DOCUMENTS

| | | | | |
|---|---|---|---|---|
| 9,526,438 | B2 * | 12/2016 | Iskander | .............. A61B 5/0816 |
| 11,253,164 | B2 * | 2/2022 | Semenov | ............. A61B 5/0042 |
| 2011/0319746 | A1 | 12/2011 | Kochba et al. | |
| 2012/0190977 | A1 * | 7/2012 | Persson | .............. G06F 18/2135 |
| | | | | 342/146 |

(Continued)

OTHER PUBLICATIONS

Abubakar, et al., "Imaging of biomedical data using a multiplicative regularized contrast source inversion method," IEEE Transactions on Microwave Theory and Techniques 50(7), pp. 1761-1771 (2002).

(Continued)

*Primary Examiner* — Lewis G West
(74) *Attorney, Agent, or Firm* — HUNTON ANDREWS KURTH LLP

(57) ABSTRACT

A system of reconstructing a dielectric image is provided. The system includes a data collection array to collect microwave scattering data. The system includes a machine learning device configured to receive the microwave scattering data, analyze the microwave scattering data, output a generated image based on the analyzed microwave scattering data, and identify at least one of a presence of disease, absence of disease, or one or more disease features from the generated image.

20 Claims, 20 Drawing Sheets

(56) References Cited

U.S. PATENT DOCUMENTS

| | | | |
|---|---|---|---|
| 2016/0287131 A1 | 10/2016 | Mccollough et al. | |
| 2017/0007148 A1* | 1/2017 | Kaditz | A61B 5/055 |
| 2017/0160363 A1* | 6/2017 | Chen | G01R 33/5608 |
| 2018/0253531 A1* | 9/2018 | Sharma | G06V 10/764 |
| 2019/0148021 A1* | 5/2019 | Styner | G06N 20/10 705/2 |
| 2019/0290162 A1* | 9/2019 | Bannister | A61B 5/0507 |
| 2019/0313937 A1* | 10/2019 | Fhager | A61B 5/72 |
| 2021/0090212 A1* | 3/2021 | Piat | G06T 3/14 |
| 2023/0237649 A1* | 7/2023 | Dillman | G16H 50/30 382/128 |

OTHER PUBLICATIONS

Agilent Technologies, "Agilent Understanding and Improving Network Analyzer Dynamic Range," Application Note 1363-1, retrieved from http://anlage.umd.edu/Microwave%20Measurements%20for%20Personal%20Web%20Site/5980-2778EN.pdf, 8 pages (2000).
Ahmed, et al., "Advanced Microwave Imaging," IEEE Microwave Magazine 13(6), pp. 26-43 (2012).
Alqadami, et al., "Wearable Electromagnetic Head Imaging System Using Flexible Wideband Antenna Array Based on Polymer Technology for Brain Stroke Diagnosis," IEEE Transactions on Biomedical Circuits and Systems 13(1), pp. 124-134 (2019).
Amineh, et al., "Three-Dimensional Near-Field Microwave Holography Using Reflected and Transmitted Signals," IEEE Transactions on Antennas and Propagation 59(12), pp. 4777-4789 (2011).
Arunachalam, et al., "A Computational Investigation of Microwave Breast Imaging Using Deformable Reflector," IEEE Transactions on Biomedical Engineering 55(2), pp. 554-562 (2008).
Belle, et al., "Big Data Analytics in Healthcare," BioMed Research International 2015:370194, 16 pages (2015).
Brown, "Electrical impedance tomography (EIT): A review," Journal of Medical Engineering & Technology 27(3), pp. 97-108 (2003).
Catapano, et al., "On Simple Methods for Shape Reconstruction of Unknown Scatterers," IEEE Transactions on Antennas and Propagation 55(5), pp. 1431-1436 (2007).
Chalouhi, et al., "Review of Cerebral Aneurysm Formation, Growth, and Rupture," Stroke 44(12), pp. 3613-3622 (2013).
Colton & Kirsch, "A simple method for solving inverse scattering problems in the resonance region," Inverse Problems 12(4), pp. 383-393 (1996).
Cooley, et al., "A portable scanner for magnetic resonance imaging of the brain," Nature Biomedical Engineering 5, pp. 229-239 (2021).
Dority & Oldham, "Subarachnoid Hemorrhage: An Update," Anesthesiology Clinics 34(3), pp. 577-600 (2016).
Fassbender, et al., "Mobile stroke units for prehospital thrombolysis, triage, and beyond: benefits and challenges," The Lancet Neurology 16(3), pp. 227-237 (2017).
Fear, et al., "Enhancing breast tumor detection with near-field imaging," IEEE Microwave Magazine 3(1), pp. 48-56 (2002).
Fei, et al., "Ultrahigh Frequency (100?MHz-300?MHz) Ultrasonic Transducers for Optical Resolution Medical Imagining," Scientific Reports 6:28360, 8 pages (2016).
Ferns, et al., "De Novo Aneurysm Formation and Growth of Untreated Aneurysms: A 5-Year MRA Follow-Up in a Large Cohort of Patients With Coiled Aneurysms and Review of the Literature," Stroke 42(2), pp. 313-318 (2011).
Gabriel, et al., "The dielectric properties of biological tissues: I. Literature survey," Physics in Medicine & Biology 41(11), pp. 2231-2249 (1996).
Gabriel, et al., "The dielectric properties of biological tissues: II. Measurements in the frequency range 10 Hz to 20 GHZ," Physics in Medicine & Biology 41(11), pp. 2251-2269 (1996).
Gabriel, et al., "The dielectric properties of biological tissues: III. Parametric models for the dielectric spectrum of tissues," Physics in Medicine & Biology 41(11), pp. 2271-2293 (1996).
Geethanath & Vaughan, "Accessible magnetic resonance imaging: A review," Journal of Magnetic Resonance Imaging 49(7), pp. e65-e77 (2019).
Giroud, et al., "The worldwide landscape of stroke in the 21st century," The Lancet 383(9913), pp. 195-197 (2014).
Gordon, et al., "Anthropometric Survey of U.S. Army Personnel: Summary Statistics, Interim Report for 1988," Defense Technical Information Center—Technical report NATIC/TR-89/027, retrieved from https://apps.dtic.mil/sti/citations/ADA209600, 335 pages (1988).
Hassanien & Kim, "Breast cancer MRI diagnosis approach using support vector machine and pulse coupled neural networks," Journal of Applied Logic 10(4), pp. 277-284 (2012).
Hemphill, et al., "Guidelines for the Management of Spontaneous Intracerebral Hemorrhage: A Guideline for Healthcare Professionals From the American Heart Association/American Stroke Association," Stroke 46(7), pp. 2032-2060 (2015).
International Search Report & Written Opinion for PCT/US2020/013204 dated Apr. 8, 2020, 8 pages.
Jamlos, et al., "High performance novel UWB array antenna for brain tumor detection via scattering parameters in microwave imaging simulation system," 9th European Conference on Antennas and Propagation (EuCAP), 5 pages (2015).
Kaatze, "Measuring the dielectric properties of materials. Ninety-year development from low- frequency techniques to broadband spectroscopy and high-frequency imaging," Measurement Science and Technology 24(1), 31 pages (2012).
Kingma & Ba, "Adam: A Method for Stochastic Optimization," 3rd International Conference for Learning Representations, retrieved from https://arxiv.org/abs/1412.6980, 15 pages (2015).
Kirsch, "Characterization of the shape of a scattering obstacle using the spectral data of the far field operator," Inverse Problems 14(6), pp. 1489-1512 (1998).
Lantigua, et al., "Subarachnoid hemorrhage: who dies, and why?," Critical Care 19:309, 10 pages (2015).
Li, et al., "Deep Learning Based Imaging Data Completion for Improved Brain Disease Diagnosis," International Conference on Medical Image Computing and Computer-Assisted Intervention 2014, pp. 305-312 (2014).
Lin & Clarke, "Microwave imaging of cerebral edema," Proceedings of the IEEE 70(5), pp. 523-524 (1982).
Meaney, et al., "A clinical prototype for active microwave imaging of the breast," IEEE Transactions on Microwave Theory and Techniques 48(11), pp. 1841-1853 (2000).
Miglioretti, et al., "The Use of Computed Tomography in Pediatrics and the Associated Radiation Exposure and Estimated Cancer Risk," JAMA Pediatrics 167(8), pp. 700-707 (2013).
Mohammed, et al., "Microwave System for Head Imaging," IEEE Transactions on Instrumentation and Measurement 63(1), pp. 117-123 (2014).
Mojabi, et al., "Microwave tomography techniques and algorithms: A review," 15th International Symposium on Antenna Technology and Applied Electromagnetics, 4 pages (2012).
Mustafa, et al., "Novel Preprocessing Techniques for Accurate Microwave Imaging of Human Brain," IEEE Antennas and Wireless Propagation Letters 12, pp. 460-463 (2013).
Nikolova, "Microwave imaging for breast cancer," IEEE Microwave Magazine 12(7), pp. 78-94 (2011).
Powers, et al., "Guidelines for the Early Management of Patients With Acute Ischemic Stroke: 2019 Update to the 2018 Guidelines for the Early Management of Acute Ischemic Stroke: A Guideline for Healthcare Professionals From the American Heart Association/American Stroke Association," Stroke 50(12), pp. e344-e418 (2019).
Salzberg, "On Comparing Classifiers: Pitfalls to Avoid and a Recommended Approach," Data Mining and Knowledge Discovery 1, pp. 317-328 (1997).
Saver, "Time is Brain—Quantified," Stroke 37(1), pp. 263-266 (2006).
Semenov & Corfield, "New Electromagnetic Methods and Applications of Antennas in Biomedicine," International Journal of Antennas and Propagation 2008:254830, 8 pages (2008).
Semenov, "Microwave tomography: review of the progress towards clinical applications," Philosophical Transactions A 367(1900), pp. 3021-3042 (2009).

(56) References Cited

OTHER PUBLICATIONS

Semenov, et al., "Microwave tomography: review of the progress towards clinical applications," Philosophical Transactions of the Royal Society A: Mathematical, Physical and Engineering Sciences 367(1900), pp. 3021-3042 (2009).

Semenov, et al., "Microwave-tomographic imaging of the high dielectric-contrast objects using different image-reconstruction approaches," EEE Transactions on Microwave Theory and Techniques 53(7), pp. 2284-2294 (2005).

Semenov, et al., "Microwave-tomographic imaging of the high dielectric-contrast objects using different image-reconstruction approaches," IEEE Transactions on Microwave Theory and Techniques 53(7), pp. 2284-2294 (2005).

Semenov, et al., "Neuroimaging patterns of cerebral hyperperfusion," Journal of Physics: Conference Series 886:012014, 5 pages (2017).

Skodvin, et al., "Cerebral Aneurysm Morphology Before and After Rupture: Nationwide Case Series of 29 Aneurysms," Stroke 48(4), pp. 880-886 (2017).

Sneth, et al., "Assessment of Brain Injury Using Portable, Low-Field Magnetic Resonance Imaging at the Bedside of Critically III Patients," JAMA Neurology 78(1), pp. E1-E7 (2020).

Stancombe, et al., "Portable Microwave Head Imaging System Using Software-Defined Radio and Switching Network," IEEE Journal of Electromagnetics, RF and Microwaves in Medicine and Biology 3(4), pp. 284-291 (2019).

Trefna & Persson, "Antenna array design for brain monitoring," 2008 IEEE Antennas and Propagation Society International Symposium, 4 pages (2008).

Van Den Berg & Kleinman, "A contrast source inversion method," Inverse Problems 13(6), pp. 1607-1620 (1997).

Wald, et al., "Low-cost and portable MRI," Journal of Magnetic Resonance Imaging 52(3), pp. 686-696 (2020).

Wang, et al., "Imaging of 3-D Dielectric Objects Using Far-Field Holographic Microwave Imaging Technique," Progress in Electromagnetics Research B 61, pp. 135-147 (2014).

Wang, et al., "Three-Dimensional Far-Field Holographic Microwave Imaging: an Experimental Investigation of Dielectric Object," Progress In Electromagnetics Research B 61, pp. 169-184 (2014).

World Health Organization, "Global Status Report on Noncommunicable Diseases 2014," retrieved from https://apps.who.int/iris/bitstream/handle/10665/148114/9789241564854_eng.pdf, 302 pages (2014).

* cited by examiner

Subject B

Subject A

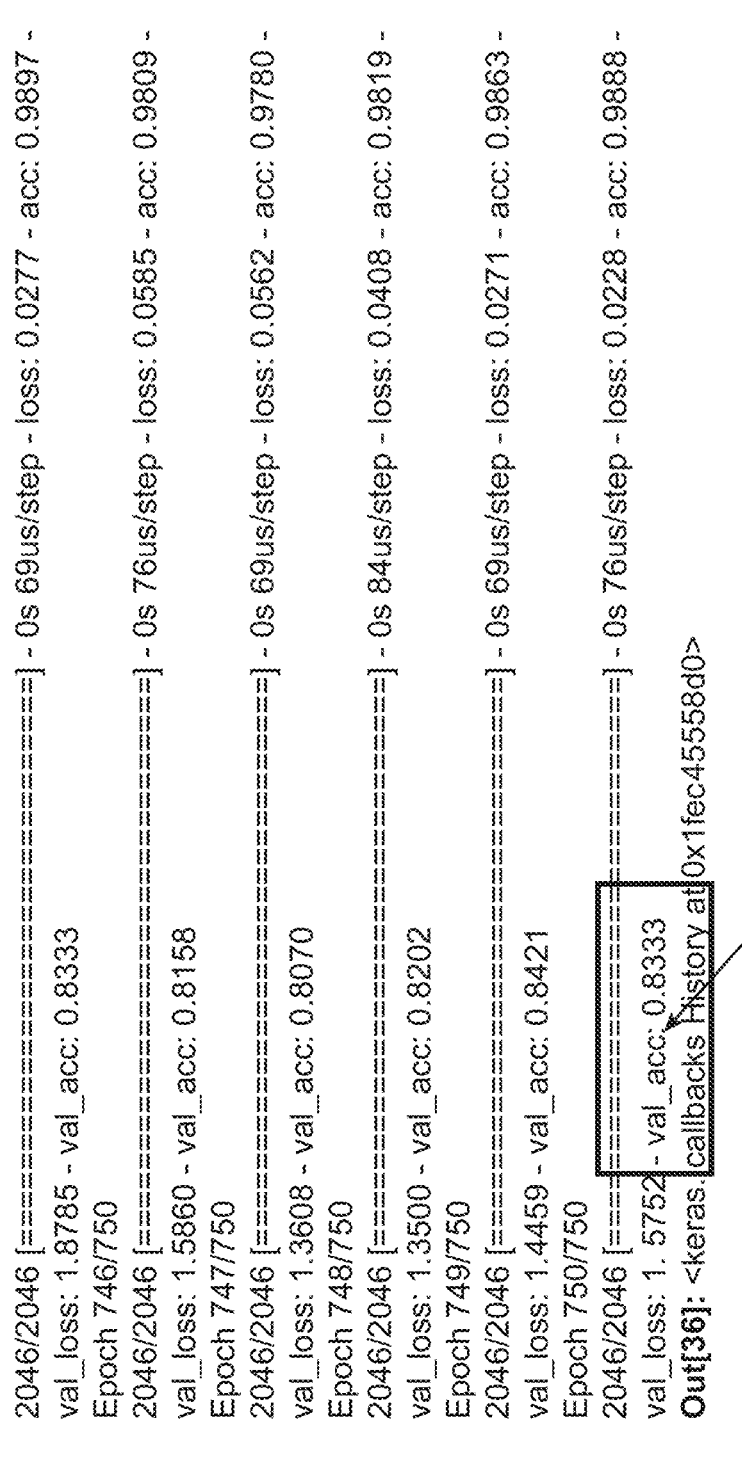

2046/2046 [==============================] - 0s 69us/step - loss: 0.0277 - acc: 0.9897 -
val_loss: 1.8785 - val_acc: 0.8333
Epoch 746/750
2046/2046 [==============================] - 0s 76us/step - loss: 0.0585 - acc: 0.9809 -
val_loss: 1.5860 - val_acc: 0.8158
Epoch 747/750
2046/2046 [==============================] - 0s 69us/step - loss: 0.0562 - acc: 0.9780 -
val_loss: 1.3608 - val_acc: 0.8070
Epoch 748/750
2046/2046 [==============================] - 0s 84us/step - loss: 0.0408 - acc: 0.9819 -
val_loss: 1.3500 - val_acc: 0.8202
Epoch 749/750
2046/2046 [==============================] - 0s 69us/step - loss: 0.0271 - acc: 0.9863 -
val_loss: 1.4459 - val_acc: 0.8421
Epoch 750/750
2046/2046 [==============================] - 0s 76us/step - loss: 0.0228 - acc: 0.9888 -
val_loss: 1.5752 - val_acc: 0.8333
Out[36]: <keras.callbacks.History at 0x1fec45558d0>

~83.3% Accuracy for detection

FIG. 4

ANT1

Back View

C7

C6

U1

Front View

SYSTEM TO DETECT DIELECTRIC CHANGES IN MATTER

CROSS-REFERENCE TO RELATED APPLICATIONS

This application is a divisional of U.S. patent application Ser. No. 17/370,983 filed Jul. 8, 2021, which is a continuation-in-part of International Application No. PCT/US2020/013204 filed Jan. 10, 2020, which claims priority to U.S. Provisional Application No. 62/791,669 filed Jan. 11, 2019. All of the above applications are incorporated herein by reference in their entirety for all purposes.

TECHNICAL FIELD

The present disclosure relates generally to methods for detecting dielectric changes in matter.

BACKGROUND

Electromagnetic (EM) waves get perturbed by the distribution and dielectric properties of tissues in the body. Microwave Tomography (MWT) technology has been developed to provide a quantitative image of the dielectric profile of an object of interest (OI). MWT techniques typically rely on two main steps: 1) a data collection step and calibration and 2) a data processing step. In the data collection and calibration step the OI is "illuminated" by multiple antennas radiating at the microwave frequencies. Data from experiments with and without the OI yielding the total field and incidence fields, respectively. The incidence field is often subtracted from the total field to yield the scattering field for which the dielectric profile of the OI is inferred in step 2. Currently, inversion algorithms utilized in MWT are nonlinear and attempt to iteratively solve the EM inverse scattering problem, and it is not possible to know, a-priori the sufficient amount of scattering data needed for proper reconstruction. To alleviate this uncertainty, as much scattering data is collected as possible. However, limitations of space in the near field system and mutual coupling between the co-resident antennas located in the MWT chamber and long acquisition time prevent increasing the number of antenna elements and acquiring of more data. The number of antenna elements is usually determined by a compromise between mechanical scanning (moving of the antenna in space) and having a large number of antennas. With this compromise in mind, it is beneficial therefore to increase the amount of information by using different boundary conditions, use of different polarizations, different sampling techniques and frequency sweeps. There are various methodologies used to calibrate the system such that measurements are stable and reconstruction noise is reduced. Once the scattering data are collected and calibrated, the data is fed into a nonlinear inversion algorithm such that the OI can be approximated. The nonlinear algorithms need to handle two important mathematical issues associated with MWT: nonlinearity and ill-posedness. Nonlinearity is handled by utilizing iterative reconstruction algorithms such as Gauss-Newton and modified gradient methods. The ill-posedness is usually handled by incorporating regularization techniques into the inversion algorithms. Many proposed algorithms have been proposed to reconstruct and pseudo-image the OI, however current state of the art MWT is not capable of routine and robust reconstruction of in vivo dielectric properties in subjects.

This prior work has focused on attempting to reconstruct a dielectric image of the patient from the limited microwave scattering. There remains a need for a process and system to utilize multiple sources, some of which may be more readily available or cheaper to procure, to provide information relating to a patient's condition. Additionally, there is a need for learning from large populations to assist with the detection of dielectric changes in matter and subjects.

SUMMARY

Embodiments described herein relate generally to a cheap, non-ionizing, portable microwave imaging system that utilizes big data and machine learning to detect the presence of disease. There remains a need for low cost, rapidly deployable, and readily scalable solutions for the evaluation of acute neurologic disorders in remote and pre-clinical settings, and thus we propose a radically different, ultrafast, plug-and-play diagnostic technology utilizing low energy radiofrequency waves to probe dielectric changes (e.g., macroscopic dielectric changes, microscopic dielectric changes, etc.) in the brain. Dielectrography, which leverages directly measurable changes in the dielectric properties of tissues to identify disease-specific "signatures" of neurologic disease. These signatures can be learned from electromagnetic scattering measurements acquired from an array of wide-band antennas operating in the conventional cellular spectrum (0.5-6 GHz), and ground truth for training dielectrographic measurements can be obtained from expert neuroimaging review (CT/MRI) occurring contemporaneously in the routine clinical setting. Physical changes in tissue electromagnetic properties (EP) caused by ischemic and hemorrhagic stroke can cause measurable changes in electromagnetic (EM) wave scattering and breakage in scattering symmetry that can be learned in a meaningful way to foster intelligent diagnoses.

Advances in supervised learning techniques enable identification of dielectrography signatures in the presence of neurological disease supporting development of a novel diagnostic instrument. The systems and methods of the present disclosure circumvent conventional underdetermined, ill-posed and non-linear challenges associated with conventional EP tomography approaches in favor of a mathematically overdetermined, biologically and clinically relevant technology.

The open source, low-cost modular design is readily scalable and ideal for large-scale dissemination. Big-data methodologies can be used to better train deep learning architectures, providing a population-wide representation of disease signatures. The fast and safe mode of operation, and high portability uniquely position dielectrography for use in conventionally unattainable high-acuity and pre-clinical environments for which urgent detection is imperative.

At least one aspect of the present disclosure is directed to a system of detecting macroscopic dielectric changes in matter. The system includes a data collection array to collect microwave scattering data. The system includes a machine learning device. The machine learning device is configured to receive the microwave scattering data, patient information, data corresponding to at least one of a presence of disease, absence of disease, or one or more disease features (e.g., size, location, texture, etc.). The machine learning device is configured to analyze the microwave scattering data, patient information, and imaging modality data. The machine learning device is configured to output at least one of a predicted disease state and predicted features based on the analyzed microwave scattering data, patient information, and imaging modality data. The machine learning device is configured to compare the imaging modality data corresponding to the at least one of the presence of disease, absence of disease, or one or more disease features to the at least one of the predicted disease state and predicted features. The machine learning device is configured to use the comparison as an input into the machine learning device.

In some embodiments, the imaging modality data comprises at least one of MR data, CT data, and PET data. In some embodiments, the machine learning device is a deep neural network machine learning device. In some embodiments, the data collection array comprises at least one of wide-band antennas and field programmable gate arrays. In some embodiments, the predicted disease state is macroscopic arrangements in dielectric properties (e.g., hemorrhage). In some embodiments, the patient information comprises at least one of patient medical history, age, dimensions of body, and sex.

At least one aspect of the present disclosure is directed to a system of reconstructing a dielectric image. The system includes a data collection array to collect microwave scattering data. The system includes a machine learning device. The machine learning device is configured to receive the microwave scattering data. The machine learning device is configured to analyze the microwave scattering data. The machine learning device is configured to output a generated image based on the analyzed microwave scattering data. The machine learning device is configured to identify at least one of the presence of disease, absence of disease, or one or more disease features from the generated image.

In some embodiments, the machine learning device is trained and validated based on patient information and imaging modality data. In some embodiments, the machine learning device is a deep neural network machine learning device. In some embodiments, the data collection array comprises at least one of wide-band antennas and field programmable gate arrays. In some embodiments, the machine learning device is configured to select a reconstruction technique based on a population size. In some embodiments, the system is integrated into a helmet. In some embodiments, the machine learning device is configured to output the predicted disease state based on one or more broadband microwave frequencies. In some embodiments, the machine learning device includes a classification network and a discrimination network.

At least one aspect of the present disclosure is directed to a method of detecting macroscopic dielectric changes in matter (e.g., structures, subjects, etc.). The method includes obtaining microwave scattering data from a data collection array. The method includes receiving, by a machine learning device, the microwave scattering data, patient information, and imaging modality data corresponding to at least one of a presence of disease, absence of disease, or one or more disease features. The method includes analyzing, by the machine learning device, the microwave scattering data, patient information, and imaging modality data. The method includes outputting, by the machine learning device, at least one of a predicted disease state and predicted features based on the analyzed microwave scattering data, patient information, and imaging modality data. The method includes comparing, by the machine learning device, the imaging modality data corresponding to the at least one of the presence of disease, absence of disease, or one or more disease features to the at least one of the predicted disease state and predicted feature. The method includes using, by the machine learning device, the comparison as an input into the machine learning device.

In some embodiments, the method includes using correlations between imaging modality data and microwave tomography to output the predicted disease state. In some embodiments, the microwave scattering data comprises at least one of S-parameter data and scattering S-parameter data. In some embodiments, the imaging modality data comprises at least one of MR data, CT data, and PET data. In some embodiments, the machine learning device is a deep neural network machine learning device. In some embodiments, the data collection array comprises at least one of wide-band antennas and field programmable gate arrays. In some embodiments, the predicted disease state is a presence of macroscopic arrangements in dielectric properties (e.g., hemorrhage). In some embodiments, the patient information comprises at least one of patient medical history, age, dimensions of body, and sex. In some embodiments, the method includes outputting the predicted disease state based on one or more broadband microwave frequencies.

It should be appreciated that all combinations of the foregoing concepts and additional concepts discussed in greater detail below (provided such concepts are not mutually inconsistent) are contemplated as being part of the subject matter disclosed herein. In particular, all combinations of claimed subject matter appearing at the end of this disclosure are contemplated as being part of the subject matter disclosed herein.

BRIEF DESCRIPTION OF DRAWINGS

The foregoing and other features of the present disclosure will become more fully apparent from the following description and appended claims, taken in conjunction with the accompanying drawings. Understanding that these drawings depict only several implementations in accordance with the disclosure and are therefore, not to be considered limiting of its scope, the disclosure will be described with additional specificity and detail through use of the accompanying drawings.

FIG. 4 shows training and validation results, according to an embodiment.

FIG. 7 shows an example PCB design of a wide-band antenna and power/voltage measurement scheme, according to an embodiment.

Figure 1:
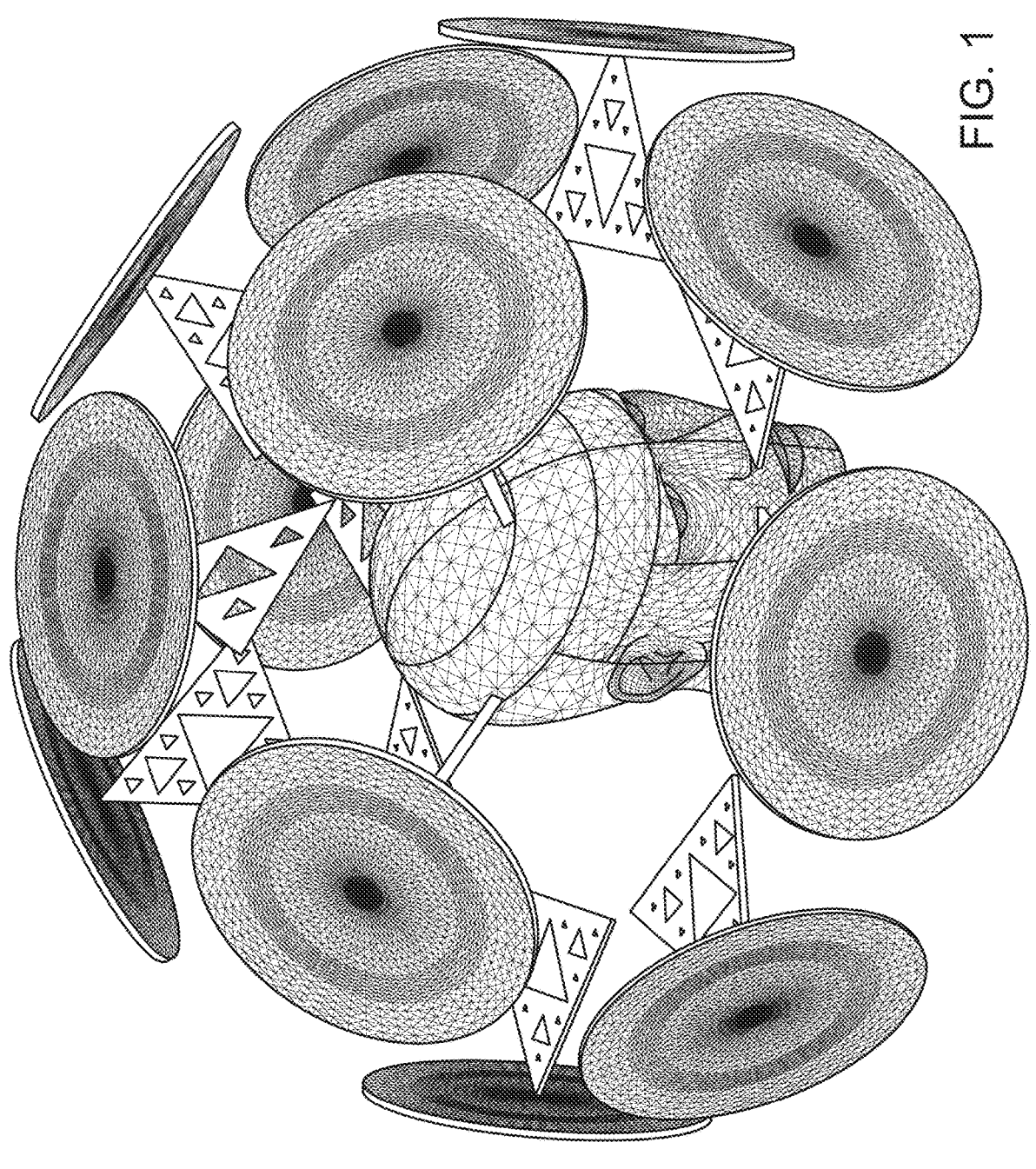
FIG. 1 shows an example of a 15-element wide-band fractal array placed around a modelled head, according to an embodiment.

Reference is made to the accompanying drawings throughout the following detailed description. In the drawings, similar symbols typically identify similar components, unless context dictates otherwise. The illustrative implementations described in the detailed description, drawings, and claims are not meant to be limiting. Other implementations may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and made part of this disclosure.

DETAILED DESCRIPTION OF VARIOUS EMBODIMENTS

EM waves get perturbed by the body. Changes in the dielectric property distribution of tissue can be altered with macroscopic changes due to disease. These diseases leave patterns or "signatures" that can be learned. Described herein are systems and processes that may utilize a multitude of information sources, combined, to detect disease. In one embodiment the process can utilize correlations between imaging data (e.g., MRI) and MWT to provide a pseudo anatomical image and can be used to learn the presence of disease and its features. Furthermore, in some embodiments, a neural net is trained to learn the best reconstruction technique, based on a sufficiently-large population size. Conventional tomography may utilize information generated from EM waves to reconstruct a three-dimensional image of electrical conductivity and relative permittivity. Studies have shown correlations between changes in the electromagnetic properties of tissues and various diseases. Electrical property (EP) tomographic imaging can be categorized as follows: 1) EP mapping leveraging magnetic field disturbances in the MRI environment. These techniques may rely on MRI machines to reconstruct the electrical conductivity and permittivity of tissue, but are impractical in mobile settings due to their weight, size, and magnetic field strengths, and are cost prohibitive (~$1M/Tesla) in many environments; 2) EP mapping using DC currents using a large number of surface detectors. The use of DC currents to estimate EP may more practical for the mobile setting, however, reconstructing EP using this methodology is ill-posed as the induced currents are localized to the surfaces of organs. Due to the inability to interrogate deep seated tissues, the diagnostic value of these techniques is limited; 3) Microwave (MW) imaging has been proposed as a pragmatic (e.g., low-cost, mobile, etc.) solution for probing electromagnetic properties employing multi-antenna MW-emitting devices at various frequencies. Microwave imaging, however, remains unable to deliver a practical diagnostic tool due to technical challenges, mainly the inherent non-linearity and ill-posedness of the inverse EP mapping reconstruction problem. Finite difference time domain (FDTD) electromagnetic field simulations software has been used to assist with the MW imaging reconstruction problem by iteratively solving Maxwell's equations on a large dataset of anatomical models, however, challenges to modeling the architectural complexity of the human brain limit its generalizability and clinical applicability. Furthermore, there remains a lack of big-data solutions to foster development of a practical and intelligent diagnostic tool equipped for learning from large population sizes.

In one embodiment, information is received from incident and scattering S-parameter measurements acquired from a multitude of antennas at different frequencies and general data such as patient history, dimensions of the body part being imaged, and more. The received information is used to help learn patterns of disease. Learning is conducted with the assistance from imaging modalities such as, but not limited to, MR, CT, PET, etc., which provide the ground truth regarding the presence of the disease as well as spatial information of the disease. Imaging modalities can include imaging modality data. For example, imagining modality data can include MR data, CT data, or PET data. Using a large dataset of patients and diseases, optimal detection of disease is possible. In some embodiments, the system includes a hardware acquisition constituted from an array of wide-band antennas and FPGA-based acquisition system, as well as a deep neural network machine learning system responsible for ascertaining the absence or presence of a disease state using a classification-type approach. As a proof of principle, in silico EM simulations were conducted to illustrate the detection of hemorrhage using the combination of the microwave imager, big data, and deep neural network.

Microwave scattering perturbations from ultra wide-band antenna arrays can be used to obtain dielectric signatures of disease. Deep neural networks (DNNs) can be used for: 1) stroke detection (e.g., classification network), and 2) characterization of the hemorrhage location and size (e.g., discrimination network). Dielectric signatures can be learned on a simulated cohort of 666 hemorrhagic stroke and control subjects using 2D stochastic head models. The classification network can yield a stratified K-fold stroke detection accuracy of 94:60%±2:86% with an AUC of 0.996, while the discrimination network can result in a mean squared error of <0.004 cm and <0.02 cm, for the stroke localization and size estimation, respectively. Microwave wide-band scattering information can be used for intelligent diagnostics.

The ongoing need for low cost, rapidly deployable, and scalable solutions for preclinical stroke diagnosis can motivate the development of novel stroke detection methods. The systems and methods of the present disclosure present a framework for hemorrhagic stroke detection using learned scattering signatures from ultra wide-band antenna arrays between 0.5 and 6 GHz. Microwave scattering perturbations can be used to learn disease signatures. Dielectric signatures of strokes can be obtained using big-data, on a population level. Deep neural networks in combination with scattering information from microwave sources can be used to classify and discriminate the presence of stroke. Results for stochastic in silico, multi-tissue head models representing the dielectric disturbances occurring in the setting of hemorrhagic stroke and derived from electromagnetic field simulations can be shown. The results can introduce an approach for intelligent diagnostics, circumventing conventional image-formation.

FIG. 1 shows an example of a 15-element wide-band fractal array placed around a modelled head. A scattering measurement at multiple frequencies can be used for detection of disease states such as stroke.

To show a proof of principle that is feasible computationally, a 2D axial model of the human head was modelled in Comsol Multiphysics 5.3 finite element modeling (FEM) solver (Burlington, MA, USA). The human bead was placed in the center of an 8-antenna structure, each radiating at twelve different frequencies between 1 GHz and 6 GHz. Using the Livelink interface to MatLab (The Math Works, Inc., Natick, Massachusetts, United States) the geometry of the 2D head and brain was altered, a slight random rotation of the head was introduced and the size/location of a hemorrhagic stroke was introduced. The following parameters were set as follows and a normal distribution between the min and the max values was used using the rand function in Matlab:

TABLE 1

| Parameter | Min | Max |
|---|---|---|
| Head Scaling Factor X (Scalar) | 0.8 | 1.2 |
| Head Scaling Factor Y (Scalar) | 0.8 | 1.2 |
| Hemorrhage (YES/NO) | 0 | 1 |
| Rotation angle (deg) | −7 | 7 |
| Blood size X (meters) | 0.01 | 0.06 |
| Blood size Y (meters) | 0.01 | 0.06 |
| Ventricle scaling X (scalar) | 0.7 | 1.3 |
| Ventricle scaling Y (scalar) | 0.7 | 1.3 |
| Brain scaling X (Scalar) | 0.8 | 1.2 |
| Brain scaling Y (Scalar) | 0.8 | 1.2 |
| Blood Location X (meters) | Minimum head size in X-size of hemorrhage in X | Maximum head size in X-size of hemorrhage in X |
| Blood Location Y (meters) | Minimum head size in Y-size of hemorrhage in Y | Maximum head size in Y-size of hemorrhage in Y |

Figure 2:
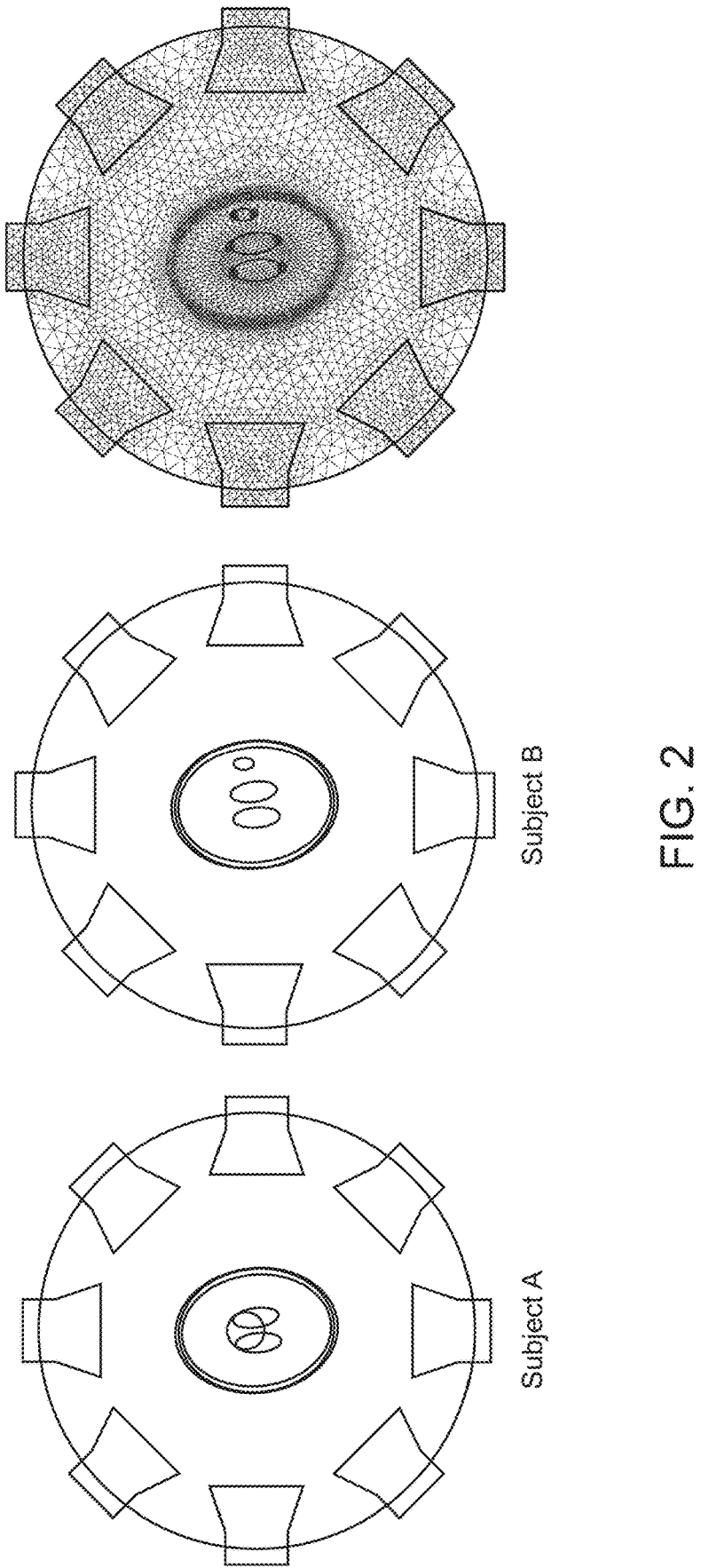
FIG. 2 shows an example of two simulated heads with of different geometries with different hemorrhage locations and sizes, according to an embodiment.

After each of these parameters was randomized in Matlab, conductivity and permittivity dielectric properties of: brain, white matter, gray matter, skull, blood and air can be assigned according to the literature values at each microwave frequency to properly simulate the EM wave propagation inside a realistic 2D head. After the tissue properties were assigned, 12 simulations can be conducted at different frequencies between 1 and 6 GHz. These twelve simulations can be conducted for each antenna in the array yielding 96 different simulations per simulated head. After the simulations converged, the complex S-parameter matrix at each frequency can be obtained yielding an 8×8×12 complex measurement matrix for each subject. Overall, ~2250 subjects can be simulated, and the presence or absence of hemorrhage can be recorded using a value of 0 or 1, respectively. FIG. 2 shows an example of two simulated heads with of different geometries with different hemorrhage locations and sizes. FEM meshing of the simulation in the middle is shown on the right.

Figure 3:
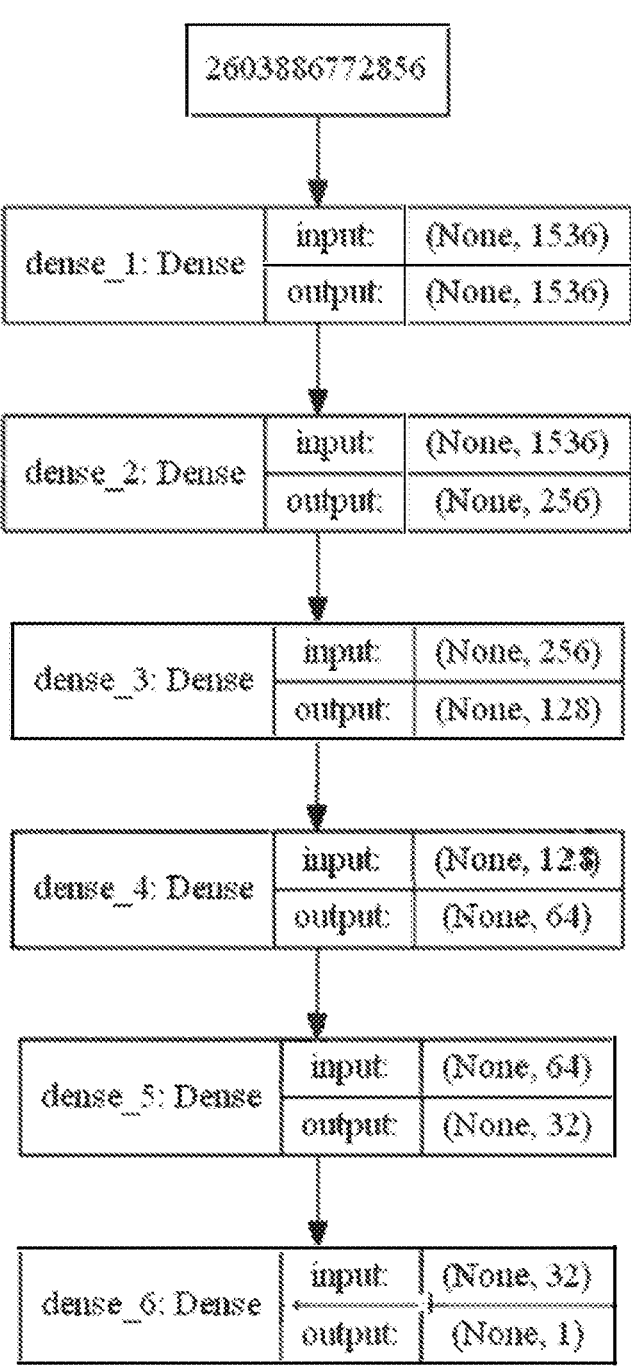
FIG. 3 shows an example deep neural network used to detect stroke from the measurement matrix, according to an embodiment.

Once all the simulations converged. The measurement matrix can be flattened, and the data can be divided into a training set of 2046 subjects and 205 for the validation set (~90% set for training). The problem can be redesigned as a binary classification problem for detection of the presence or absence of hemorrhage. FIG. 3 shows an example deep neural network used to detect stroke from the measurement matrix.

Detection accuracy on the validation set can be ~83%. Further improvement can be implemented by changing the neural network architecture, optimization of hyperparameters, incorporation of patient information such as age, medical history, dimensions of body, sex, etc. Age related change in dielectric properties of tissues were not included in these simulations and can possibly improve the real-life detection accuracy. FIG. 4 shows training and validation results.

Figure 5:
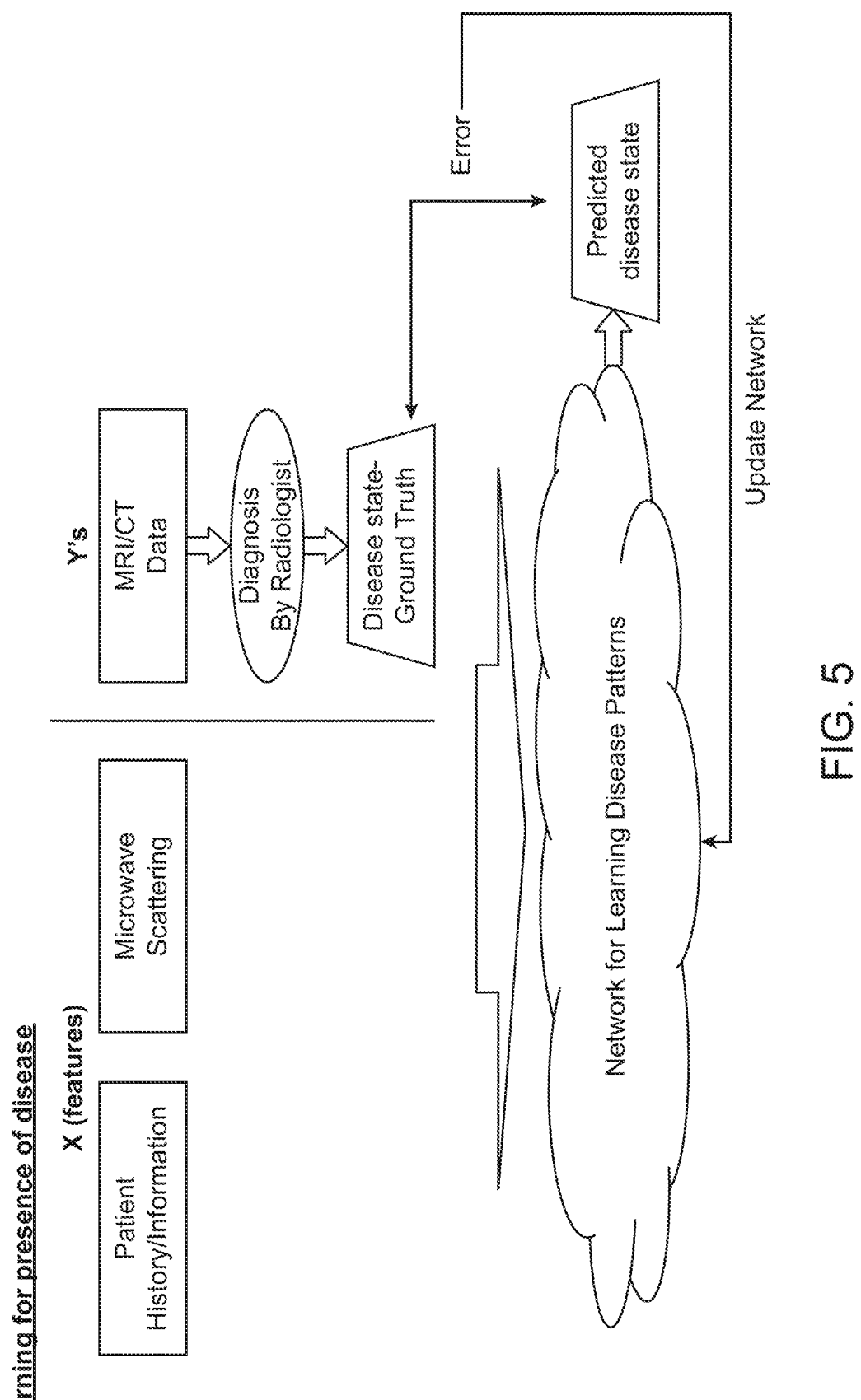
FIG. 5 shows utilization of the Maxwell detector for detection of the presence of disease, according to an embodiment.

In one embodiment, network A, the detection of disease is defined as a classification problem. As shown in FIG. 5, a patient is scanned using the Maxwell detector and thereafter an MRI is obtained. The MRI/CT diagnosis is then used for the training Y's as the ground truth of the disease. Once the network is trained and validated, the Maxwell detector, alone, can be used to detect a disease state, without the MRI/CT.

Figure 6:
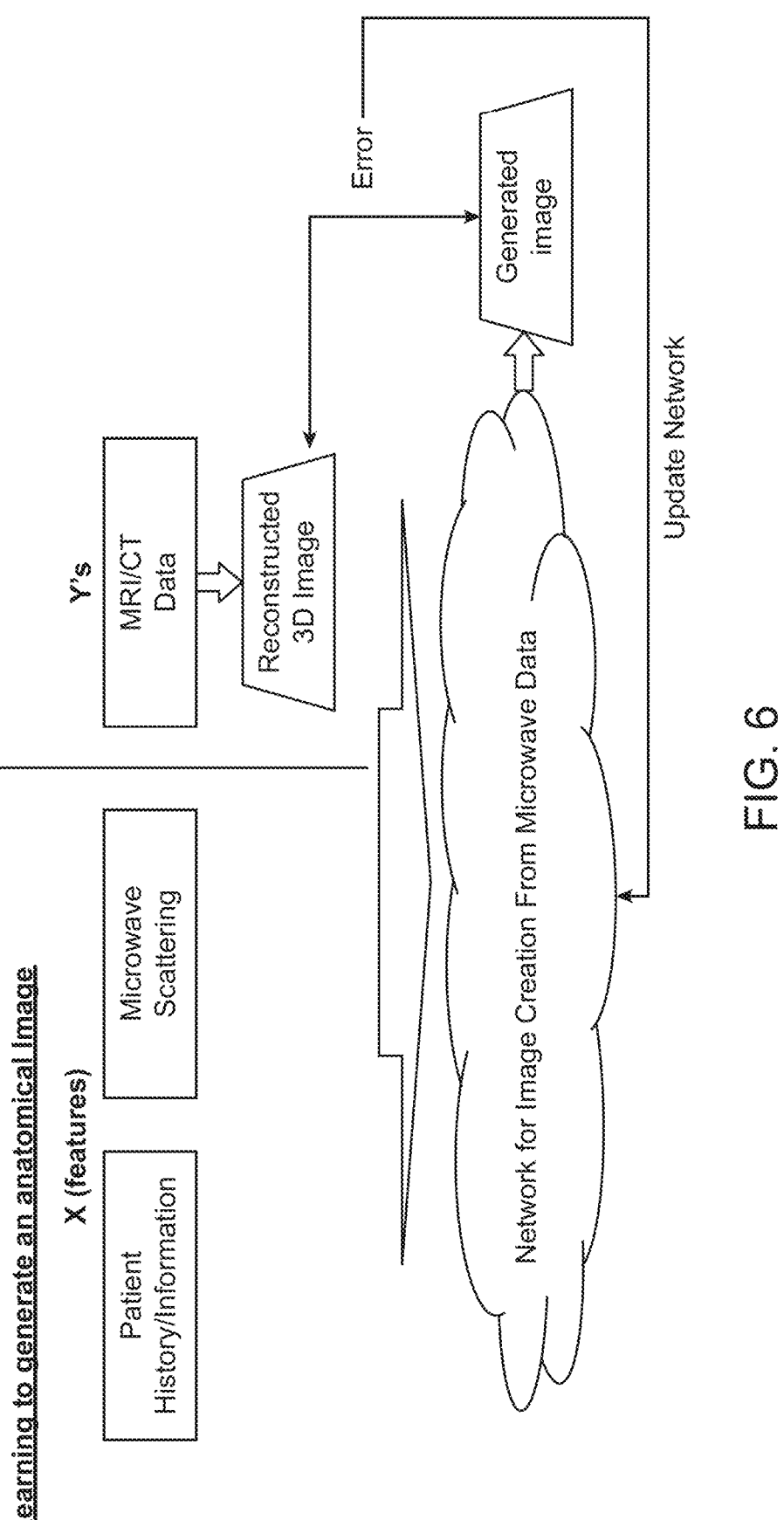
FIG. 6 shows utilization of the MRI/CT image for accurate reconstruction of the OI dielectric image, according to an embodiment.

In a second embodiment, network B shown in FIG. 6, utilizes image information from MRI/CT to jointly reconstruct a dielectric image. This network takes the approximated microwave image (which is ill-posed) and the known MRI/CT image and utilizes it to reconstruct a dielectric image of the OI. Utilization of the MR data for training a network that jointly reconstructs a dielectric image, can improve the fidelity of the reconstruction. Once the neural network is defined, trained, and validated, the Maxwell detector can be used independently to create a dielectric image of the OI.

Figure 7:
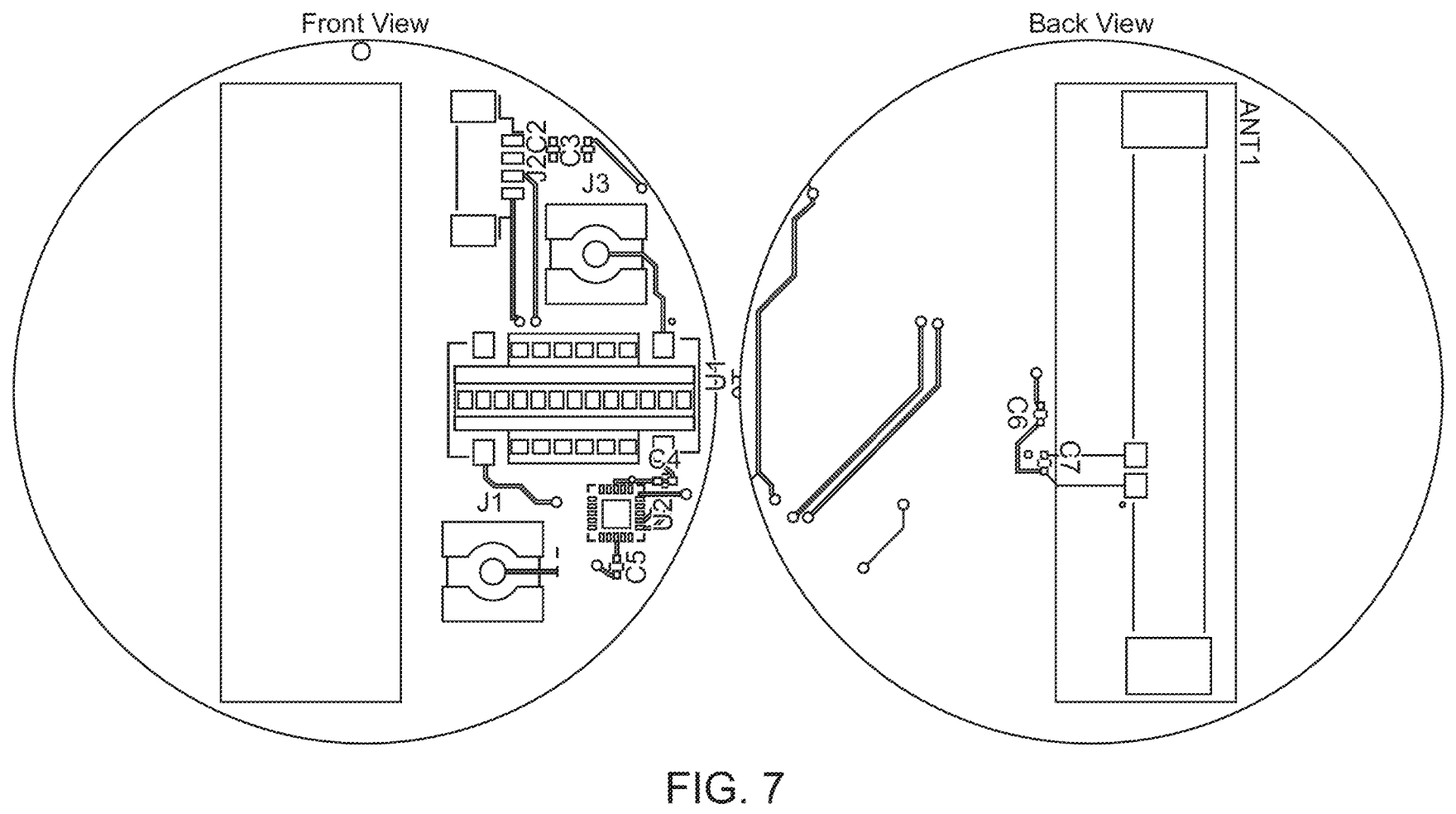

FIG. 7 is an example PCB design of a wide-band antenna and power/voltage measurement scheme. The PCB includes RF switches, directional coupler, antennas, connectors, isolation elements fitting onto a puck design with diameter of 5 mm. Elements of this design can be placed in a helmet that may be used for dielectrography measurements.

Figure 8:
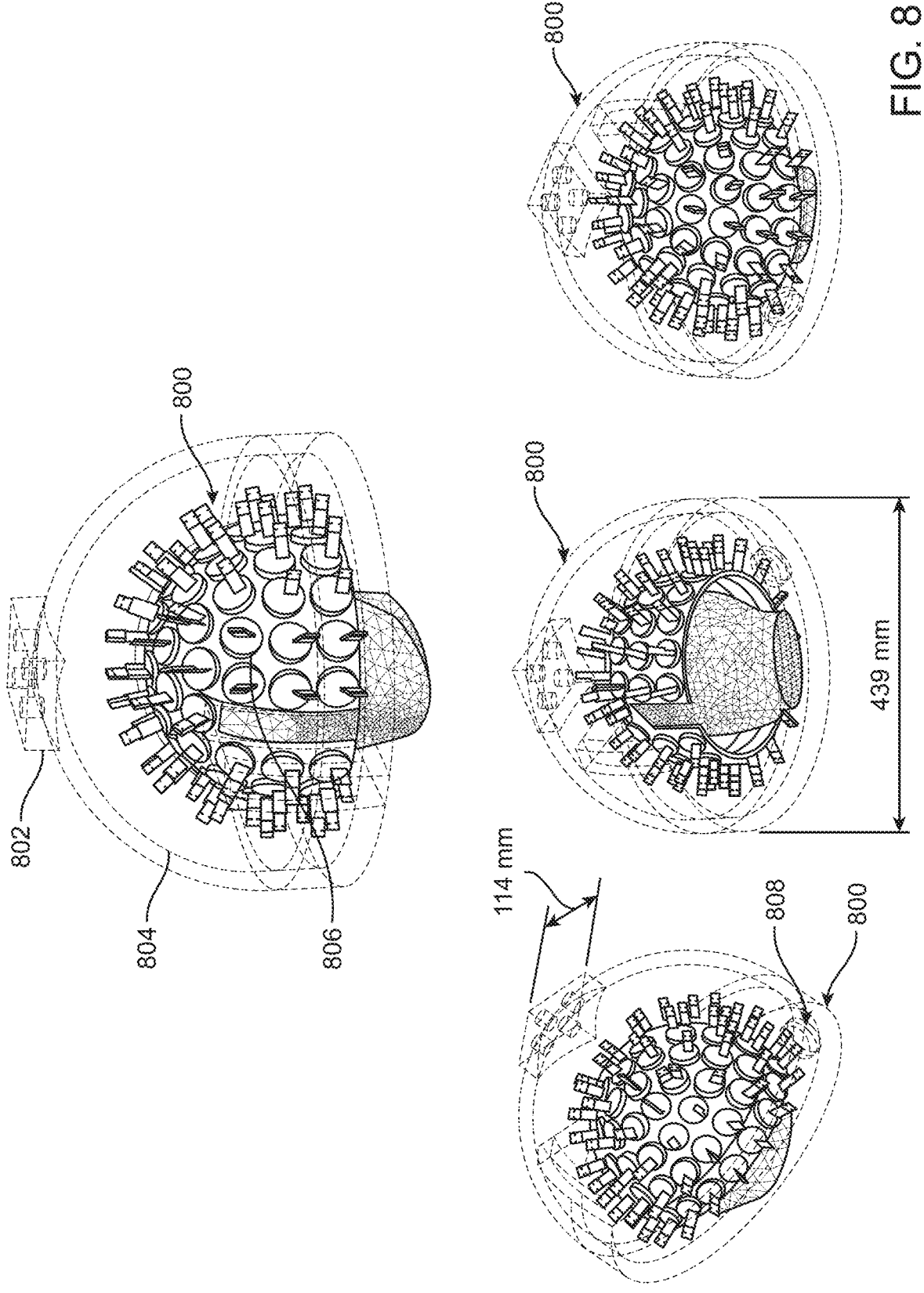
FIG. 8 shows an example helmet incorporating the systems and methods of the present disclosure, according to an embodiment.

FIG. 8 is an example helmet according to the systems and methods of the present, disclosure. The helmet 800 can include a mounting setup 802. The helmet 800 can be a modular design. For example, analog to digital conversion can be conducted on antennas using software defined radio (SDR). SDR can be used to minimize interferences, improve antenna isolation and provide improved scatter measurements. The helmet 800 can include a copper shielding layer 804. The copper shielding layer 804 can mitigate external interferences. The helmet 800 can include a patch antenna 806. The patch antenna 806 can include a directional patch antennal or an ultra-wide band directional patch antenna. The patch antenna 806 can be disposed on a high-dielectric substrate. A plurality of antennas can be disposed inside the helmet 800 to interface with a head. For example, 70 antennas can be disposed inside the helmet 800 to interface with the head. The helmet 800 can include an output port 808. The output port 808 can include a digital signal output port.

The helmet 800 can facilitate rapid, nearly real-time (<10 seconds) acquisition and may be powered from a conventional AC outlet. The helmet 800 is safe for routine use as it has a maximum output power of a mobile phone making it suitable for pre-clinical, high-acuity and biologically harmless longitudinal assessment and monitoring. The helmet 800 can be equipped with a fully modular, 70-antenna configuration leveraging advances in radio-frequency (RF) electronics and acquisition strategies allowing use of ultra-wide-band (UWB) detector design and maintenance of high sensitivity to dielectric disturbances at varying depths. In some embodiments, dielectrography does not rely on ionizing radiation, strong magnetic field, or user dependence. This user-independence and relief from the demands of technical and medical expertise can vastly broaden the reach of diagnostic medical technology, increasing accessibility and practicality of early, advanced diagnosis in underserved areas.

Figure 9:
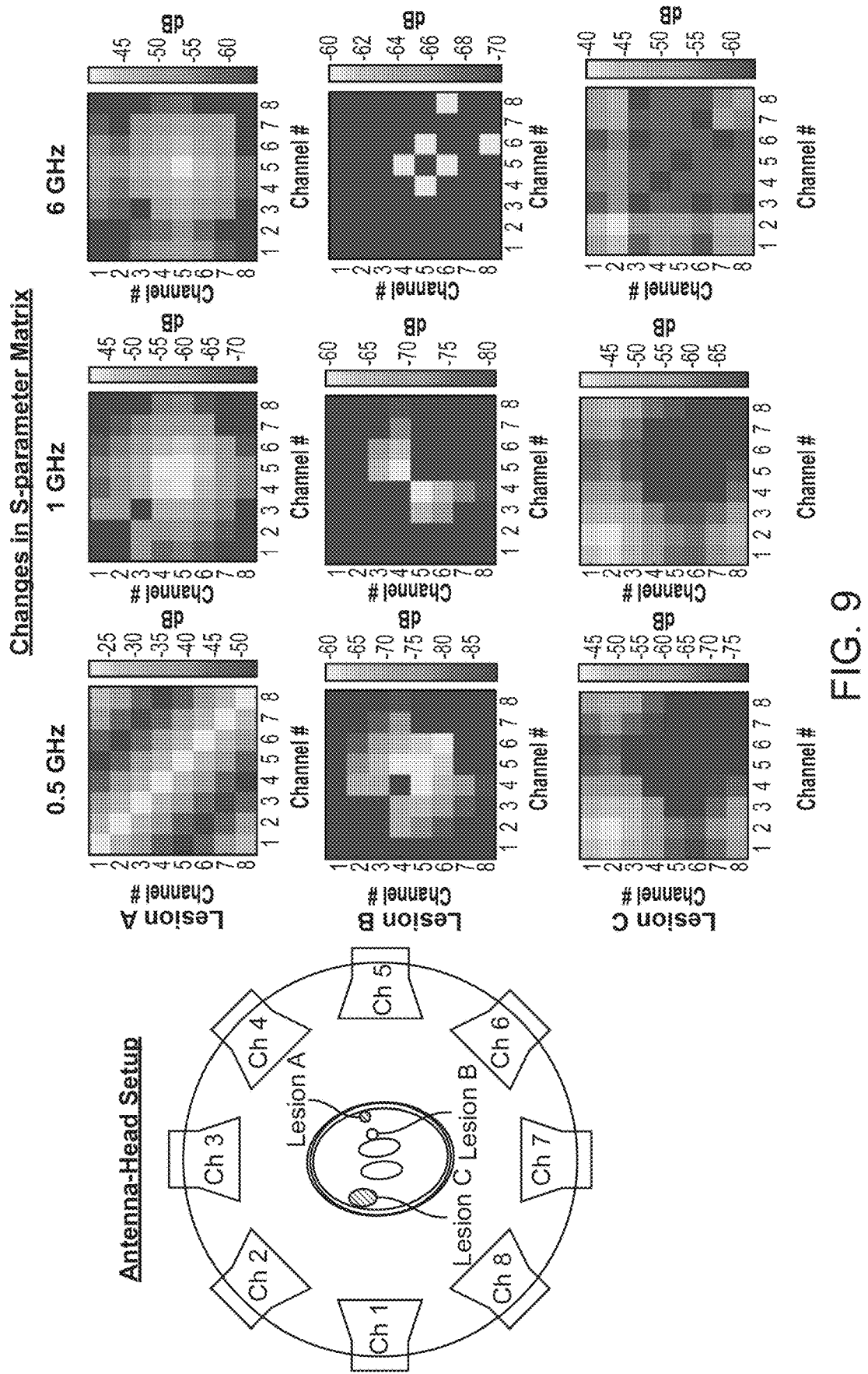
FIG. 9 shows an example of changes in the scattering (S)-parameter matrix coefficients are simulated for a modeled hemorrhagic lesion (blood) in three locations, according to an embodiment.

FIG. 9 shows an example of changes in the scattering (S)-parameter matrix coefficients are simulated for a modeled hemorrhagic lesion (blood) in three locations. FIG. 9 demonstrates the change in the scattering (S) parameter matrix as a function of frequency and location/size of a hemorrhage within a modeled human head. The changes are roughly $10^4\times$ greater than the signals detectable in MRI (~150 dBm), thus not requiring low-noise pre-amplification. Lesion A shows a small superficial lesion exhibiting greater specificity at higher frequencies. The highest changes occurred at the intersection of antennas 4 and 5, represented in S45, S54, and S55. The lesion in A was moved anteriorly, represented by Lesion B, producing changes in the S-parameter matrix which can be seen to vary across different frequencies. A larger lesion, represented by Lesion C, was introduced at the intersection of antennas 1 and 2, producing changes in S12, S21 and S22 at all frequencies. All meaningful changes were >70 dB, well within the dynamic range of the SDR ADC and DAC specifications. Signals are on the order of 10,000× compared to MRI signals (~150 dBm).

The observed changes in the S-parameters for three different strokes (represented as ovals A, B and C) are summarized in FIG. 9 for different frequencies. Lesion A can exhibit prominent changes in the S-parameters adjacent to antennas 4 and 5 occurring above 0.5 GHz. The change in S45 can represent the increase in power transfer between antennas 4 and 5 occurring due to the changes in dielectric parameters in the brain induced by the presence of stroke. When the same-sized lesion (lesion B) is displaced to a deeper region of the brain, changes in the S-parameters of channels 4, 5 and 6 can be observed at the 0.5 GHZ, as well as at higher frequencies. A larger lesion C, in the contralateral side (relative to strokes A and B), changed the S-parameter values for channels 1 and 2 (closest to lesion C) and their respective coupling.

Figures 10A, 10B, 10C:
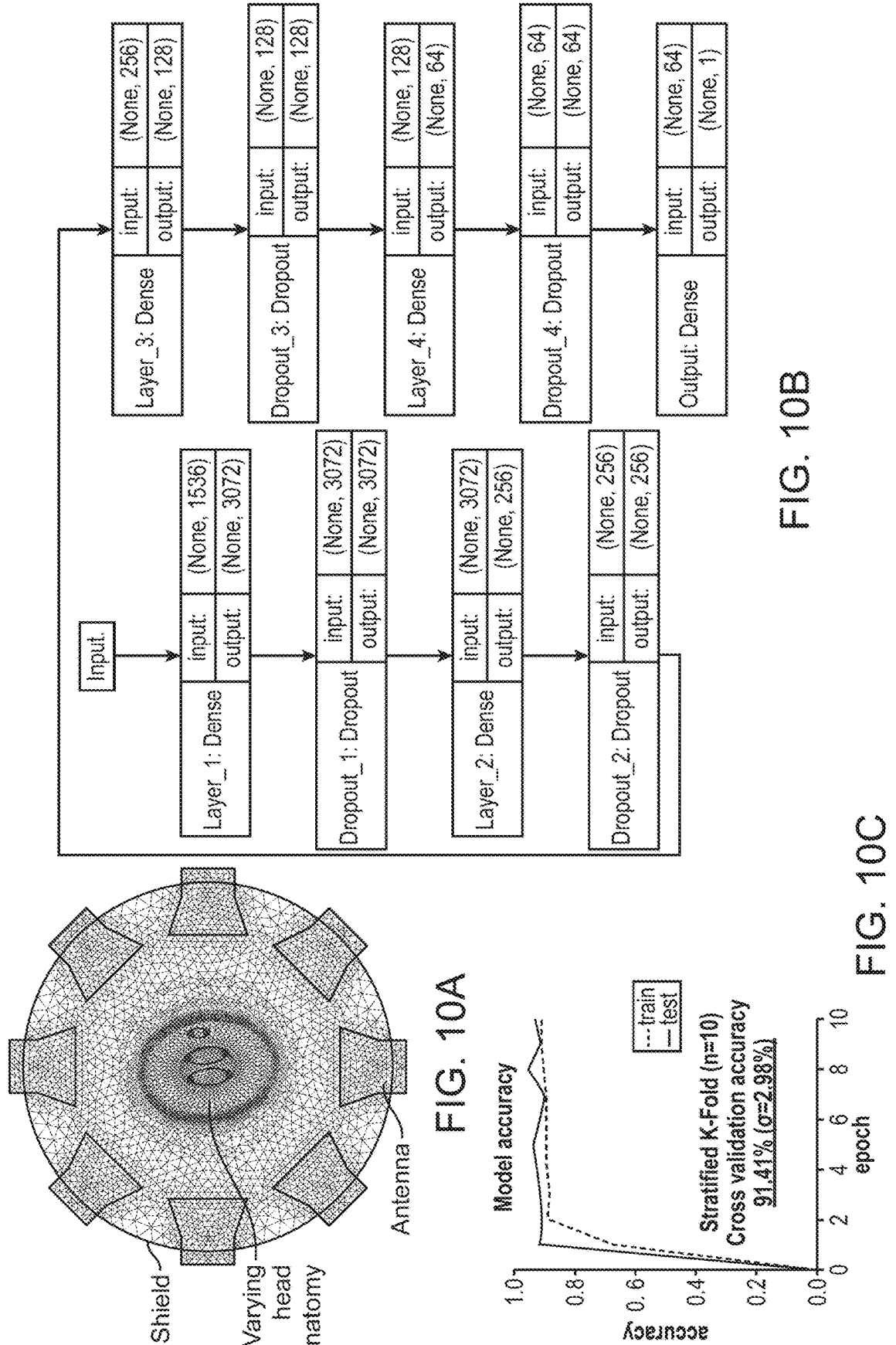
FIGS. 10A-C show in silico validations, according to an embodiment.

FIG. 10 shows in silico validations. For example, 652 subjects' heads were modelled with different distributions of dielectric properties. For 50% of those subjects, blood in the brain was introduced, simulating hemorrhagic stroke condition. Stroke size was between 1 cm and 5 cm (in x and y independently, forming an oval shape). Tissues were meshed using a Finite Element solver (A). Simulations were conducted for each antenna and 12 different frequencies between 0.5 and 6 GHz, yielding 62,592 electromagnetic simulations conducted in total, taking ~1 month to compute on a 24 core EM field simulation server. Simulated scattering measurements and the presence or absence of hemorrhagic stroke were fed into a deep neural net (network architecture shown in B). Ten percent of the data was used for validation. Model accuracy is shown in C. K-fold cross validation accuracy was 91.4% with standard deviation of 2.98%.

Figures 11A, 11B, 11C:
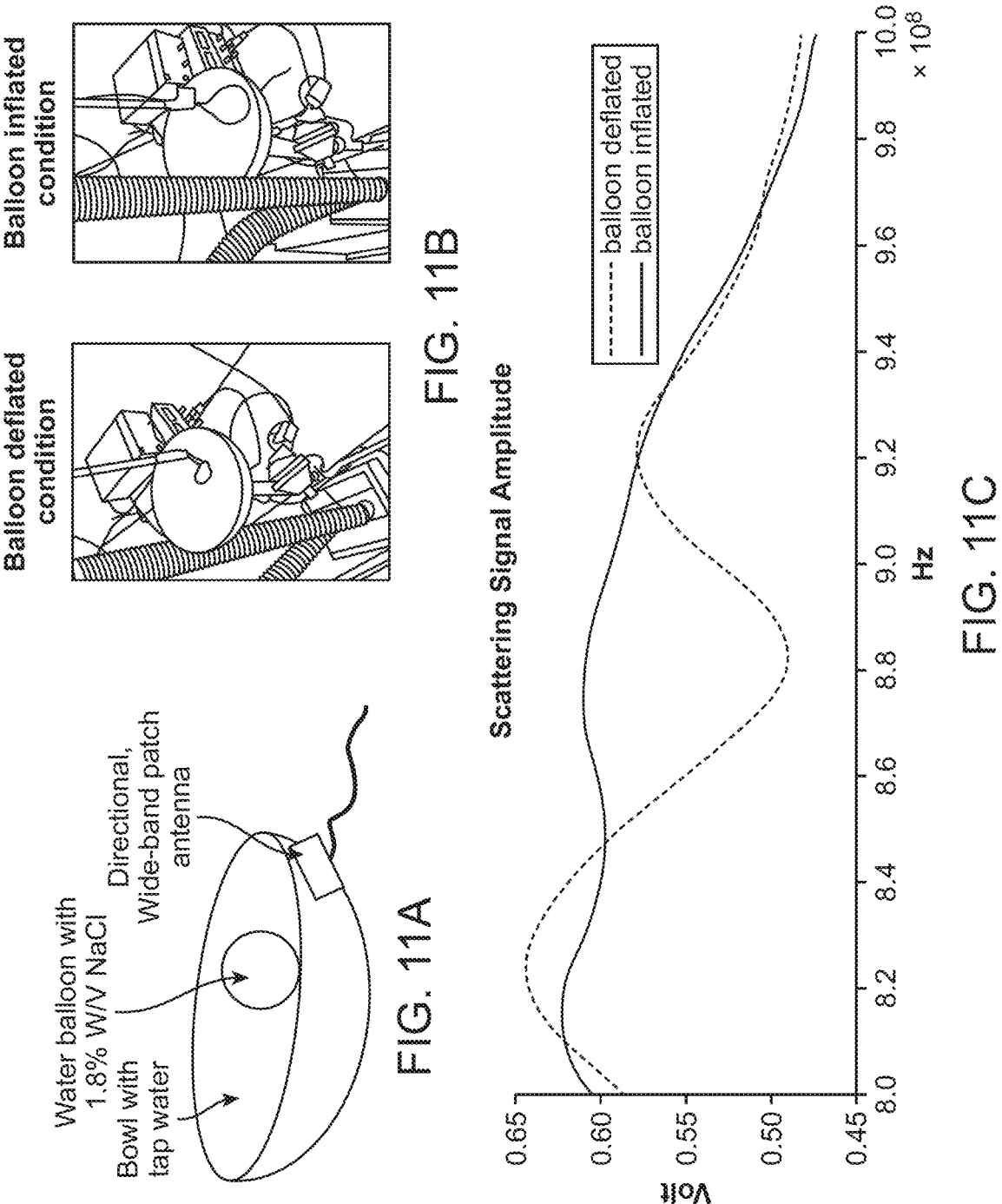
FIGS. 11A-C show single-antenna dielectrography measurements demonstrated in a phantom setup, according to an embodiment.

FIG. 11 shows single-antenna dielectrography measurements demonstrated in a phantom setup. A directional patch antenna was placed adjacent to a plastic bowl (made of ABS) filled with tap water (A). The antenna was connected to a network analyzer and was excited between 800 MHz and 1 GHz. Two conditions were imposed (shown in B): 1. A balloon was deflated to minimally perturbed that scattering of the electromagnetic waves emanating from the antenna. 2. The balloon was inflated with water and 1.8% W/V NaCl simulating blood. Amplitude and phase scattering results measured on a network analyzer are shown in C.

In some embodiments, the system uses multi-layered deep neural networks with a softmax layer. One example of the advantage of using AI in a supervised learning approach is that patterns of disease can be learned from the imaging data, and neural nets are quite well suited for that. Reinforcement learning techniques or conventional deep neural nets can be used to solve the classification problem that may be used to diagnose a certain medical condition. Encoder-decoder network architectures can be used to solve the tomographic problem where an image is reconstructed. There is a pressing need for safe, low cost, rapidly deployable, and readily scalable solutions for the evaluation of acute neurologic disorders in remote and pre-clinical settings, and thus radically different, ultrafast (e.g., <10 seconds per scan), plug-and-play diagnostic technology is proposed herein, utilizing low energy radiofrequency waves to probe macroscopic dielectric changes in the brain. This technique is referred to as dielectrography, leveraging known and directly measurable changes in the dielectric properties of tissues to identify disease-specific "signatures" of neurologic disease. These "signatures" can be learned using AI from electromagnetic scattering measurements acquired from an array of wide-band antennas operating in the conventional cellular spectrum (700 MHz-6 GHZ), and ground truth for training dielectrographic measurements can be obtained from expert neuroimaging review (CT/MRI) occurring contemporaneously in the routine clinical setting.

In one embodiment the system is very portable, thus being capable of being deployed in ambulances, military bases, and third world countries that cannot afford state of the art imaging machines such as MRIs and CT. The Maxwell detector can be "fine-tuned" to detect a wide array of diseases provided there is a gross-change in the dielectric properties of tissues.

In one embodiment, the system can be used to assess hydrocephalus in adults and children, traumatic brain injury identification and progression assessment, and other conditions were there are macroscopic changes to the dielectric tissue distribution that are different than in the underlying population.

Mapping electrical properties (EP) is an area of active research as changes in the EP of tissues correlate with macroscopic disease (e.g., strokes, cancer, etc.). Fast, mobile and low-cost techniques often employ scattering measurements from microwave (MW) sources to map EP of tissues. MW imaging however fails to deliver due to non-linearity and ill-posedness of the inverse reconstruction problem. In on embodiment, these challenges are mitigated by: 1) Rather than producing EP images from underdetermined data, the problem is transformed to an overdetermined classification problem easier to solve; 2) Neural networks and stochastic gradient decent-like techniques are used to overcome non-linear challenges; 3) Big data is used for learning disease "signatures" in a large cohort of patients; and 4) Scattering measurements are conducted over a wide-range of frequencies, which are sensitive to dielectric disturbances at different depths and improve acuity to discern disease states.

Unique attributes of the proposed design include its small form factor, low power, low-cost, portability, lack of ionizing radiation, acquisition speed, and intelligent diagnostic capabilities making it ideally suited for use in rapid response and high acuity contexts, and for both initial and longitudinal diagnostic evaluation.

Microwave tomography (MWT) has historically faced two main challenges: 1) non-linearity of the reconstruction, handled unsuccessfully by iterative reconstruction techniques (e.g., Gauss-Newton), and 2) ill-posedness (e.g., the number of measurements is significantly smaller than the number of unknowns). These conditions defy robust solutions through conventional algorithms; however, the maturation of AI, assimilation of big data and the resources to learn from large populations, and advances in RF electronics supporting fast acquisitions and capacity to conduct broadband frequency excitations can be exploited to enable high performance in vivo MWT. While the conventional MWT problem is underdetermined and conventional regularization (e.g., L1) techniques are employed for image reconstruction, here the problem was relaxed to disease classification, which is computationally better conditioned and biologically relevant. Together with utilization of AI and big-data, the untapped potential of dielectrography can reach full realization. In silico verification of this approach has been confirmed with highly promising results.

In early silico proof-of-concept investigations, a 6-layer deep neural net was utilized to determine the presence or absence of disease. In these trials, the last layer of the neural network had a sigmoid activation function to support a binary classification and a binary cross-entropy loss function was used to drive learning. Alternative approaches may include Decision Trees. Naïve Bayes Classifier Algorithm, etc. that can enhance performance of the classifier.

In one embodiment, the AI model can utilize electromagnetic scattering measurements and patient history, which can be abstracted from anonymized electronic medical records archived for all patients in the system, as model inputs. At the same time, imaging diagnosis, namely the presence of neurological disease (attained from MRI/CT) can be used to train a deep neural network classifier to detect the presence or absence of disease. In exploratory in situ simulations, a deep neural net with 6 fully connected layers correctly detected stroke with ~85% accuracy on a limited training/ test set (including merely 12 frequency measurements). Conventional classification metrics can be used to ensure generalization. Once generalized, the system design and network coefficients can be made openly available (open source) for the benefit of the community. The application can be further expanded to include a broader gamut of neurologic disease, once the framework is implemented and matured.

Figure 12A:
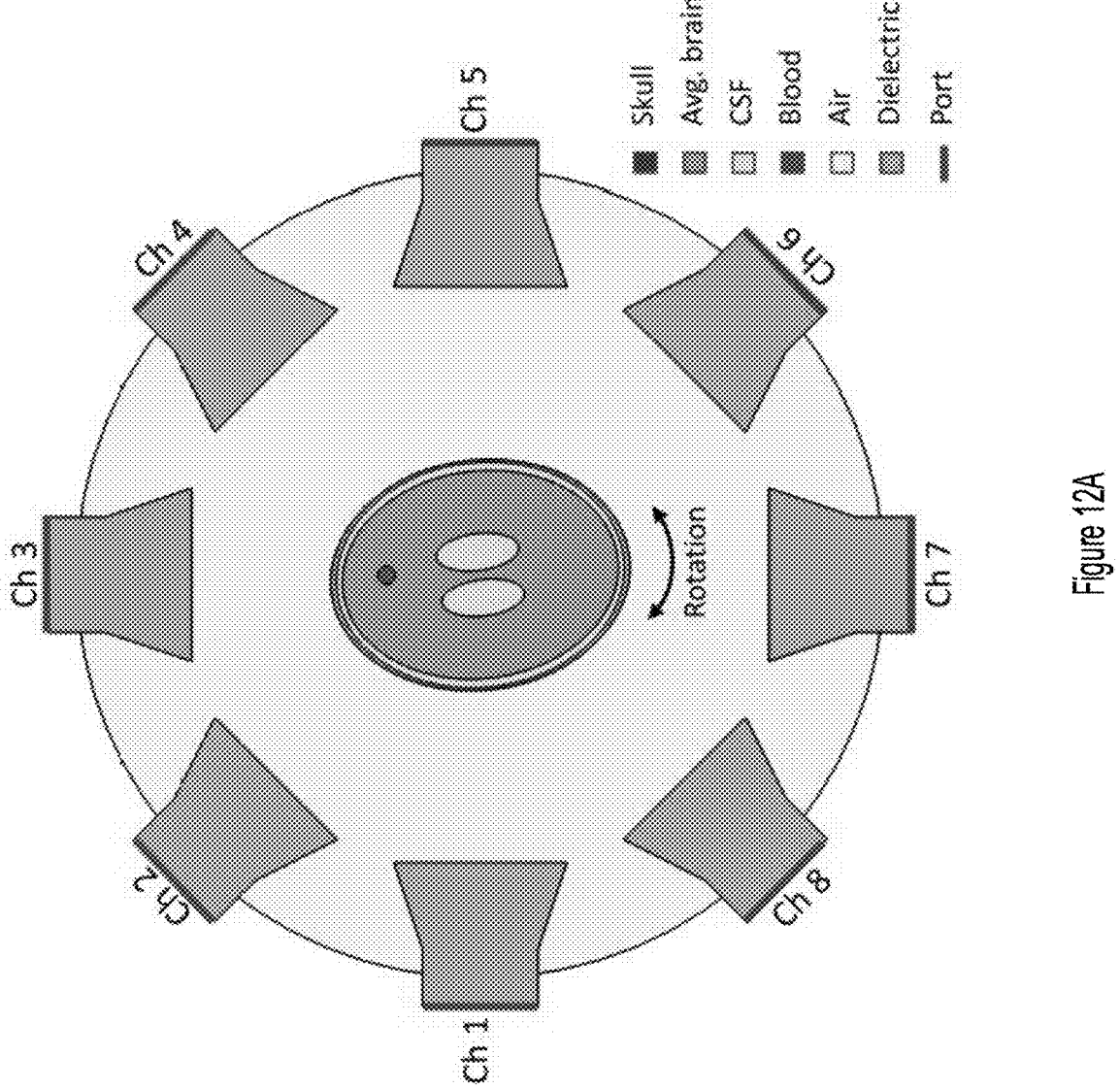
FIG. 12A shows a simulation setup for an FEM solver, according to an embodiment.

FIG. 12A shows a simulation setup for an FEM solver. Eight horn antennas can be placed around varying 2D multi-tissue head model. Simulations can be conducted using the COMSOL finite element method (FEM) software (COMSOL Multiphysics, Burlington, MA USA) on an array of 8 wide-band horn antennas, each with an aperture of 120 mm and driven using a waveguide excitation. Each antenna can be placed azimuthally around bead models at 45 degree increments and filled with a dielectric with relative permittivity of 50 to reduce the cutoff frequency. A two-dimensional (2D) solver can be used to reduce computational time as a large number of simulations can be necessary for varying anatomy-coil-frequency conditions. Simulations can be conducted by alternating with a single active port while recording the voltage on every port to calculate the S-parameter matrix at each frequency. A stationary frequency domain direct solver using the Newton method can be used to ensure convergence. A total of 20 frequency sweeps can be conducted at equal increments between 0.5 and 6 GHz and can be prescribed to inform DNNs trained for classification and discrimination of stroke. After the simulations conclude, random Gaussian noise with mean zero and standard deviation of −100 dBm can be added to the S-parameters. This noise can be introduced to represent the noise floor in commonly-used network analyzers and can be incorporated in a system design to acquire S-parameters for stroke detection. For each head simulation, a complex matrix with dimension equal to the (number of channels)× (number of channels)×(number of frequencies) can be obtained. EM field computations and post-processing can be executed on a simulation workstation with a dual-core Xeon E5-2630 CPU with 128 GB of RAM.

A total of 666 head models can be generated in simulation using COMSOL Livelink, enabling scripting within the Matlab (Mathworks, Natick, Massachusetts USA) environment. A 2D synthetic, trans-axial slice through the brain, can be modeled based on the 3D Specific Anthropomorphic Mannequin (SAM) model to produce a simulated central slice through the brain at the level of the lateral ventricles. Stochastic modifications to the brain dimensions can be applied to each head model that include variation in the width and length of the head and brain independently, and width and length of the lateral ventricles. The head models can be placed centrally within the antenna array, with random reorientation of the head prescribed relative to the array, to represent varying bead orientations occurring when the head is fixated to a plastic stereotactic frame permitted to pivot relative to the antenna array, yet remain immobile with respect to translation. Variations in head anatomy and rotation are summarized in Table 2.

TABLE 2

| Anatomy | Orientation | Mean | Std. | Min | Max | Unit |
|---|---|---|---|---|---|---|
| Head size | x-direction | 20 | 2 | 13.8 | 25.6 | cm |
| | y-direction | 26 | 2.6 | 19.8 | 33.0 | cm |
| Vent size | x-direction | 4.55 | 0.5 | 5.9 | 3.5 | cm |
| | y-direction | 8.45 | 0.85 | 10.8 | 6.34 | cm |
| Head rot. | xy-plane | 0 | 3.5 | −10.76 | 10.18 | deg. |
| Blood size | x-direction | 2 | 0.5 | 0.84 | 3.8 | cm |
| | y-direction | 2 | 0.5 | 0.84 | 3.8 | cm |

A total of five different tissues can be included in the simulations: skull, blood, cerebrospinal fluid (CSF), average brain, and air. For each frequency of interest between 0.5 and 6 GHz, the dielectric properties can be extracted. Random-valued head anatomies can be fed to the DNN representing subject-wise variation of the head, thus presenting the DNN with highly varying conditions that disrupt the S-parameter matrices to facilitate learning. Fifty percent of the heads can be selected at random and intracranial blood can be introduced in random locations, simulating intraparenchymal hemorrhagic strokes. Sizes of the strokes can be independently varied in the x- and y-directions with a 2±0.5 cm (mean±standard deviation) in diameter (ranging between 0.5 and 4 cm, in the x- and y-directions, independently) (Table 2). The stroke x- and y-locations can be selected from a uniform random distribution, with the outer bounds of the distribution changing depending on the size of the brain. A total of 106,560 simulations can be conducted using different head anatomies, frequency sweeps, and antennas driven. Execution of these simulations can be performed in >720 continuous hours of simulation time.

Figure 12B:
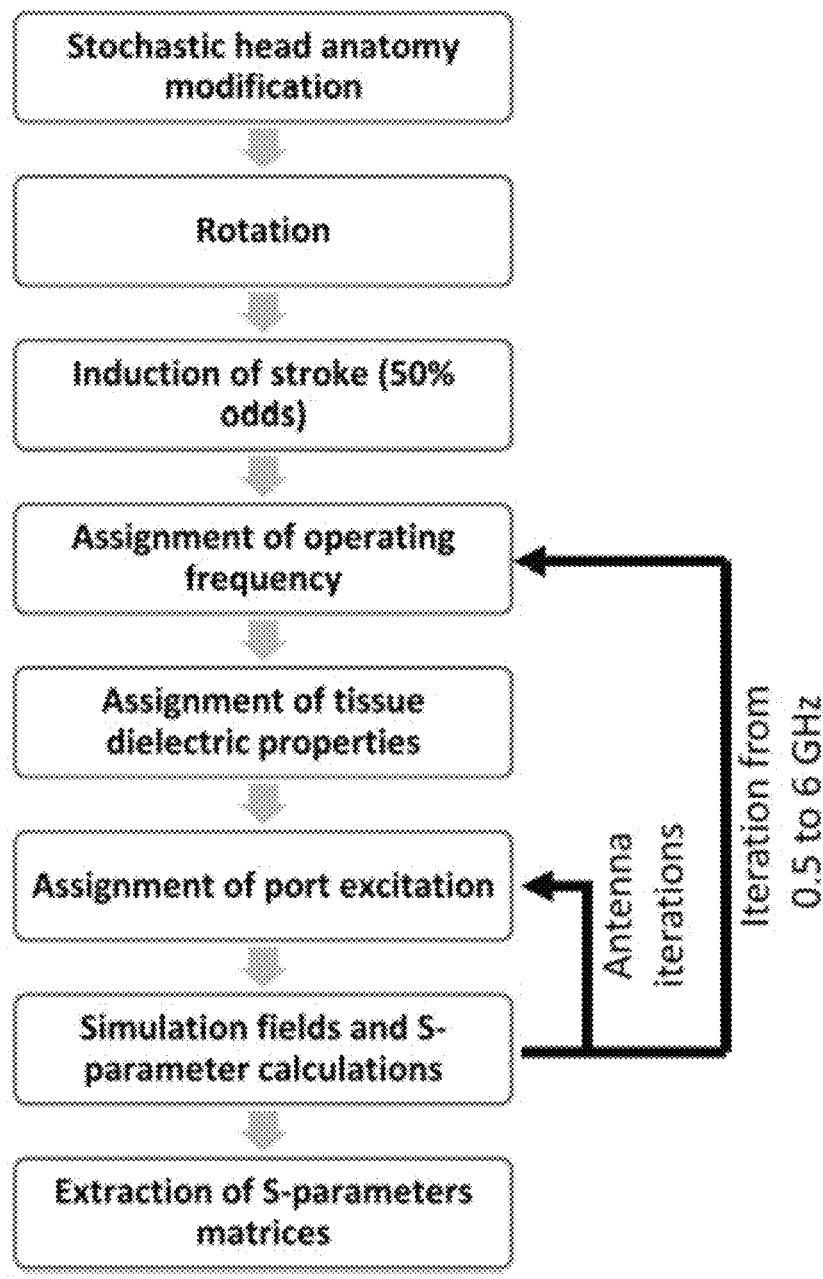
FIG. 12B shows a flow chart for processing of EM field simulations, according to an embodiment.

FIG. 12B shows a flow chart for processing of EM field simulations, allowing modification of the head models, dielectric properties, and induction of stroke, simulating different frequencies and excitations. The pipeline for stochastic head model simulations and computation of the S-parameter matrices at each frequency of operation is summarized in FIG. 12B. The effect of perturbations on the dielectric properties of the head induced by different strokes was analyzed and plotted across different frequencies.

Multi-frequency S-parameter matrices can be exported into python. The dimensions of each complex-valued matrix can be $n_{ch} \times n_{ch} \times n_f$, where $n_{ch}$ is the number of channels and $n_f$ is the number of simulated frequencies. Amplitude and phase of the complex-valued matrices can be reformatted, for each model, to $n_{ch2} * n_f$. Training, testing, and validation of the neural net models can be conducted in the Keras environment. Before training, the data across subjects can be split such that 70% of the data are used for training, 15% for validation, and 15% for testing, respectively. Training, testing, and validation data sets can be normalized using a scalar normalizer such that the data was scaled to unit variance. Two distinct DNNs can be used for the stroke diagnosis: the first DNN can be used to classify the presence of hemorrhagic stroke using S-parameter matrix data ("Classification DNN") and the second DNN can be used to discriminate the stroke location and size inside the head ("Discrimination DNN").

Figure 13:
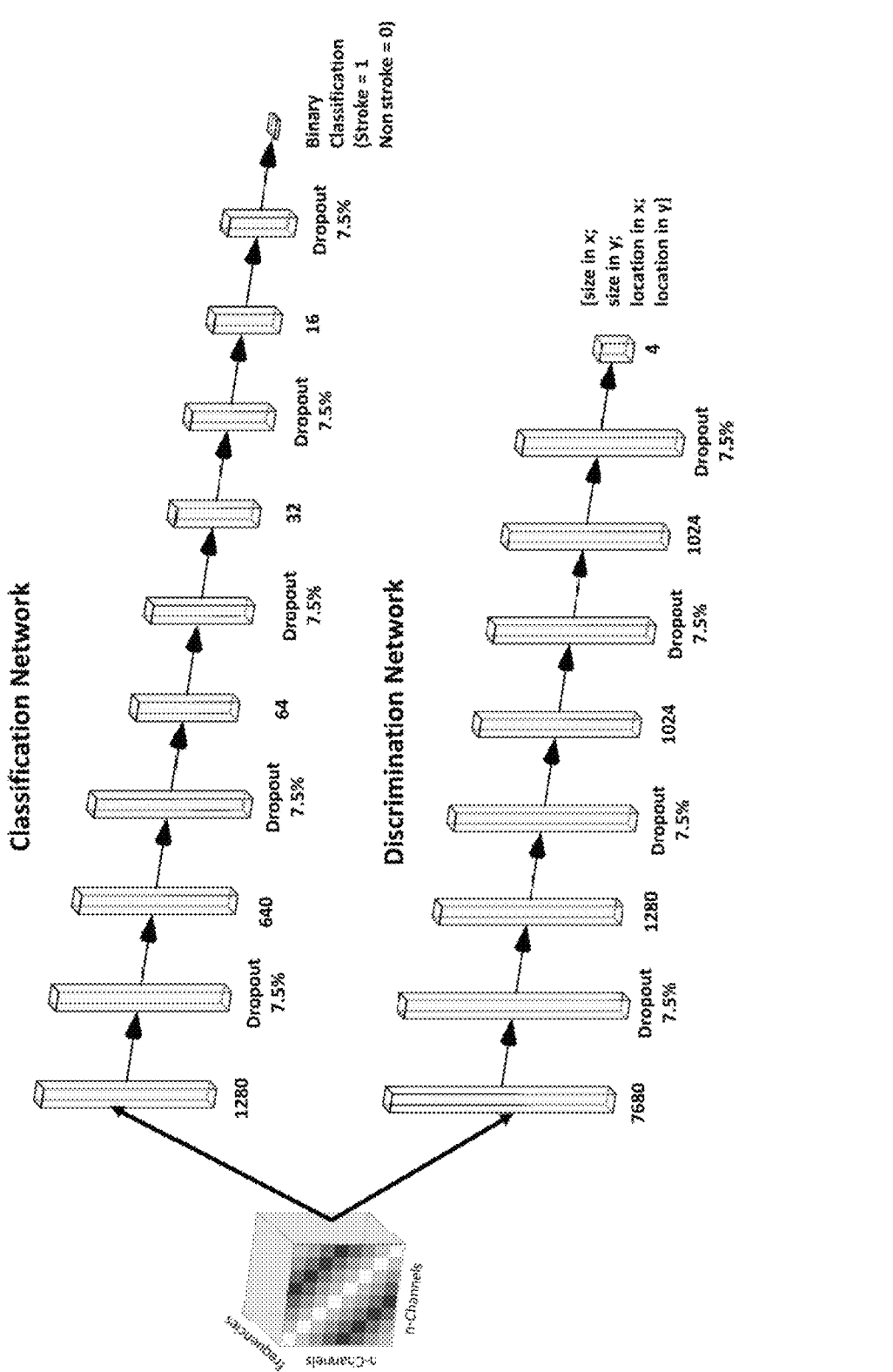
FIG. 13 shows DNN architectures used for the classification and discrimination networks, according to an embodiment.

FIG. 13 shows DNN architectures used for the classification and discrimination networks. Amplitude and phase of the multi-frequency S-parameter matrices can be concatenated, vectorized and fed into each DNN. A sigmoid output and 4-vector linear output were used for the classification and discrimination networks, respectively. The classification DNN can be trained using 666 stroke and control head models, consisting of 307 simulated strokes (46%). The discrimination DNN can be trained using the stroke-only cohort. A graphical depiction of the classification DNN comprising fully-connected layers followed by a final sigmoid activation layer is shown in FIG. 13, top. Input to the classification network can include 1280 unique parameters (generated from the complex s-parameter matrices) and an input layer for the classification network accordingly set with the purpose of identifying frequency dependent coil-coupling relationships that are unique for identification of stroke. The discrimination DNN can include a wider fully-connected architecture terminating in a 4-dimensional linear layer with the 4-dimensional vector representing the x-, y-locations and size of hemorrhage in the x- and y-directions, respectively, thus characterizing the dimension and location of the hemorrhage, FIG. 13, bottom.

For both the classification and discrimination networks, a dropout layer with dropout threshold of 7.5% can be introduced between the fully connected layers to reduce overfitting. Each layer of the classification network can be initialized using a truncated normal distribution with zero mean and standard deviation of 0.75 and the discrimination network can be initialized using a truncated normal distribution with zero mean and standard deviation of 0.05. Model optimization for both networks can be performed using the Adam optimizer. A binary cross-entropy loss function with 20 epochs and a batch size of 100 can be used for the classification network training, while a mean square error (MSE) loss function, 1000 epochs, and a batch size of 100 can be used for discrimination network training. The loss function and accuracy of each trained network as a function of epoch can be plotted. Classification accuracy can be quantified using the stratified K-fold method with 10 splits. A Receiver-Operating Characteristic (ROC) curve can be plotted and the area under the curve (AUC) can be computed. The discrimination network can be evaluated by calculation of the test-set MSE for the errors in predicted x-location and y-location and x-stroke size and y-stroke size. For visualization purposes, results can be compared against the ground truth in randomly-chosen stroke models selected from the test-set. Frequency-dependent stroke dielectric effects and antenna-dependent stroke dielectric effects can be assessed by plotting changes in the magnitude of the S-parameter matrices occurring due to the presence of stroke for 0.5, 1 and 3 GHz and presented dB scale.

Figure 14A:
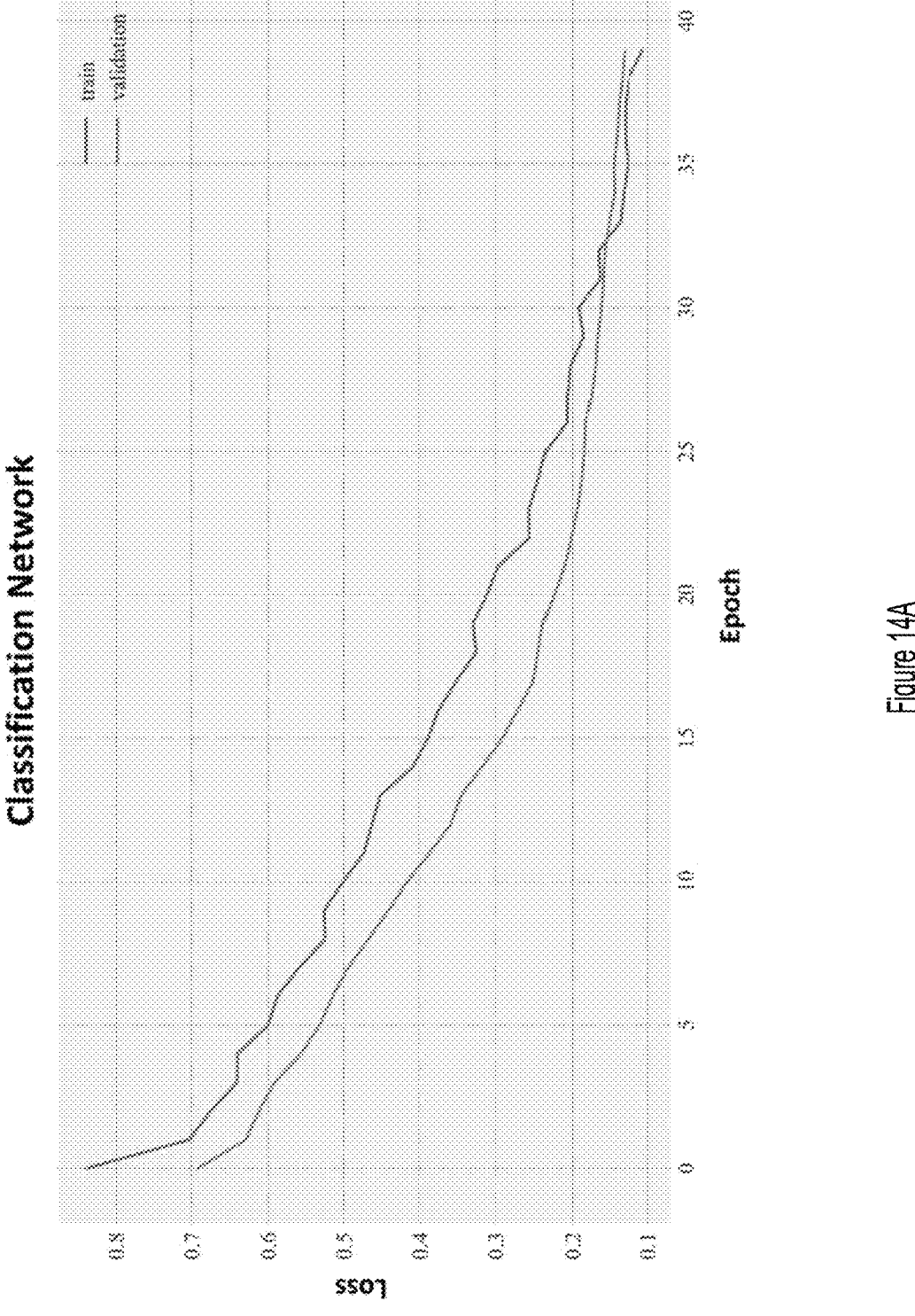
FIG. 14A shows classification network loss as a function of epoch number for the training and validation sets, according to an embodiment.

FIG. 14A shows classification network loss as a function of epoch number for the training and validation sets. Execution of the classification network training can be performed and the binary cross-entropy loss as a function of epoch can be plotted, demonstrating convergence of the network.

The discrimination network can be designed to predict both the size and location of the stroke. Discrimination can be performed via learning patterns from frequency dependent S-parameters from different antenna elements, rather than relying on conventional microwave imaging reconstruction. To better discriminate stroke spatial characteristics, a larger network with more redundancy can be used which can include a 6× larger first layer, compared to the classification network, and a relatively larger number of neurons in the subsequent hidden layers, permitting finer prediction of size and location (FIG. 13, bottom).

Figure 14B:
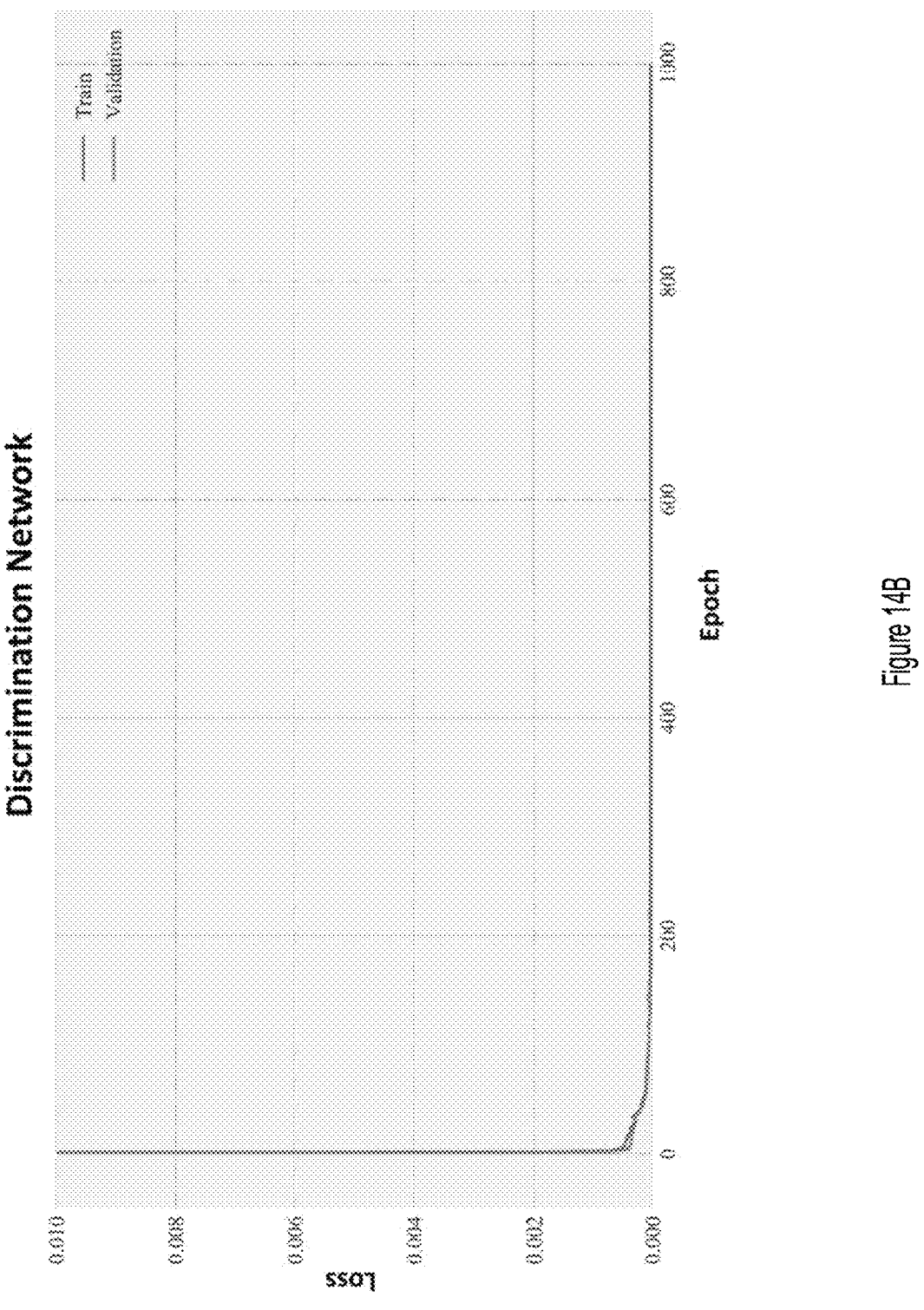
FIG. 14B shows training discrimination network MSE as a function of epoch number for the stroke-only training and validation sets, according to an embodiment.

FIG. 14B shows training discrimination network MSE as a function of epoch number for the stroke-only training and validation sets. The discrimination network MSE as a function of epoch is shown in FIG. 14B, demonstrating close agreement between the test and validation set errors.

Figure 15A:
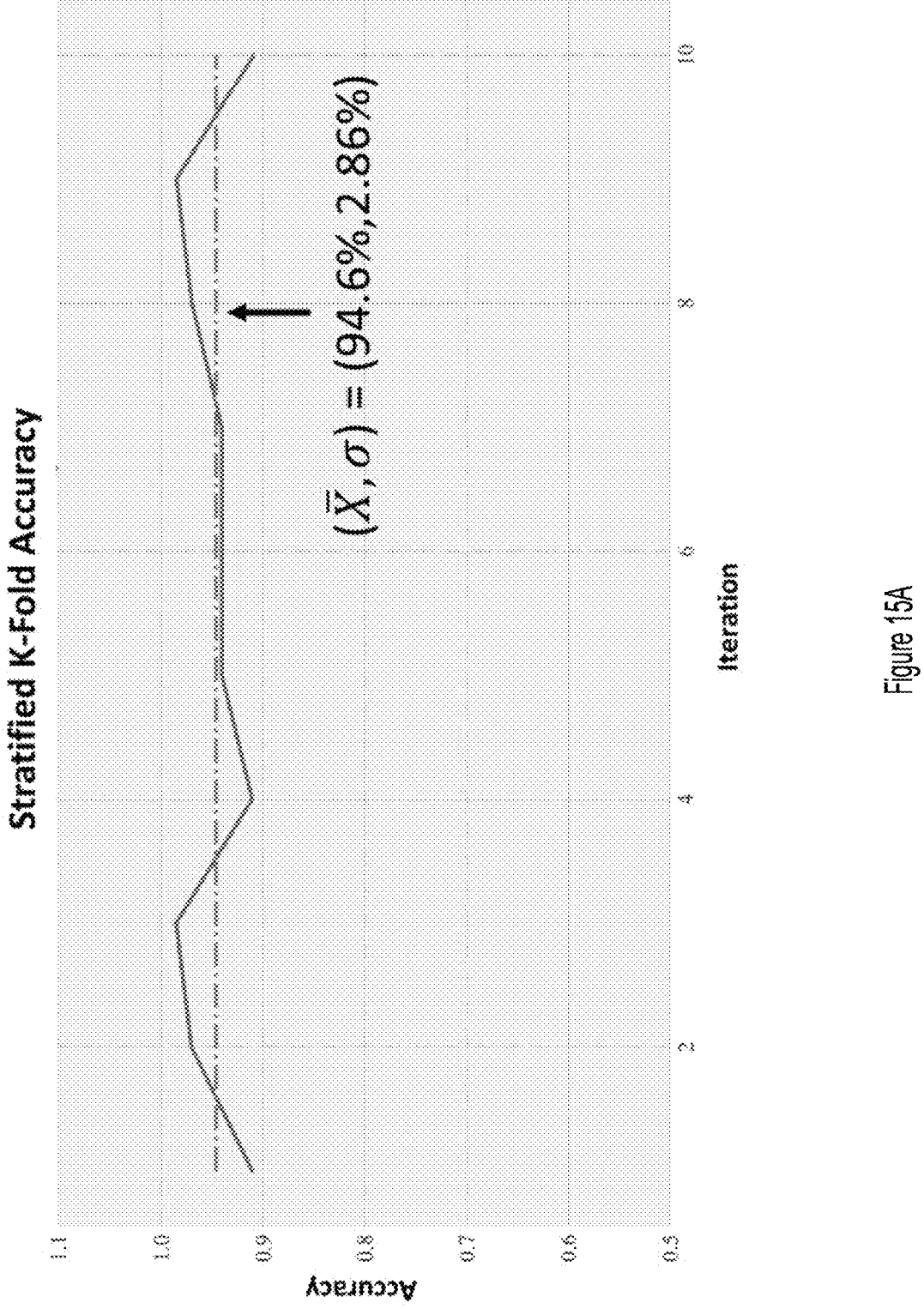
FIG. 15A shows stratified K-fold accuracy as a function of iteration for the classification network and mean and standard deviation, according to an embodiment.

FIG. 15A shows stratified K-fold accuracy as a function of iteration for the classification network and mean and standard deviation. Generalization can be evaluated using the stratified K-fold method, exhibiting a mean model accuracy of 94.6% with a standard deviation of ±2.86% (FIG. 15A).

Figure 15B:
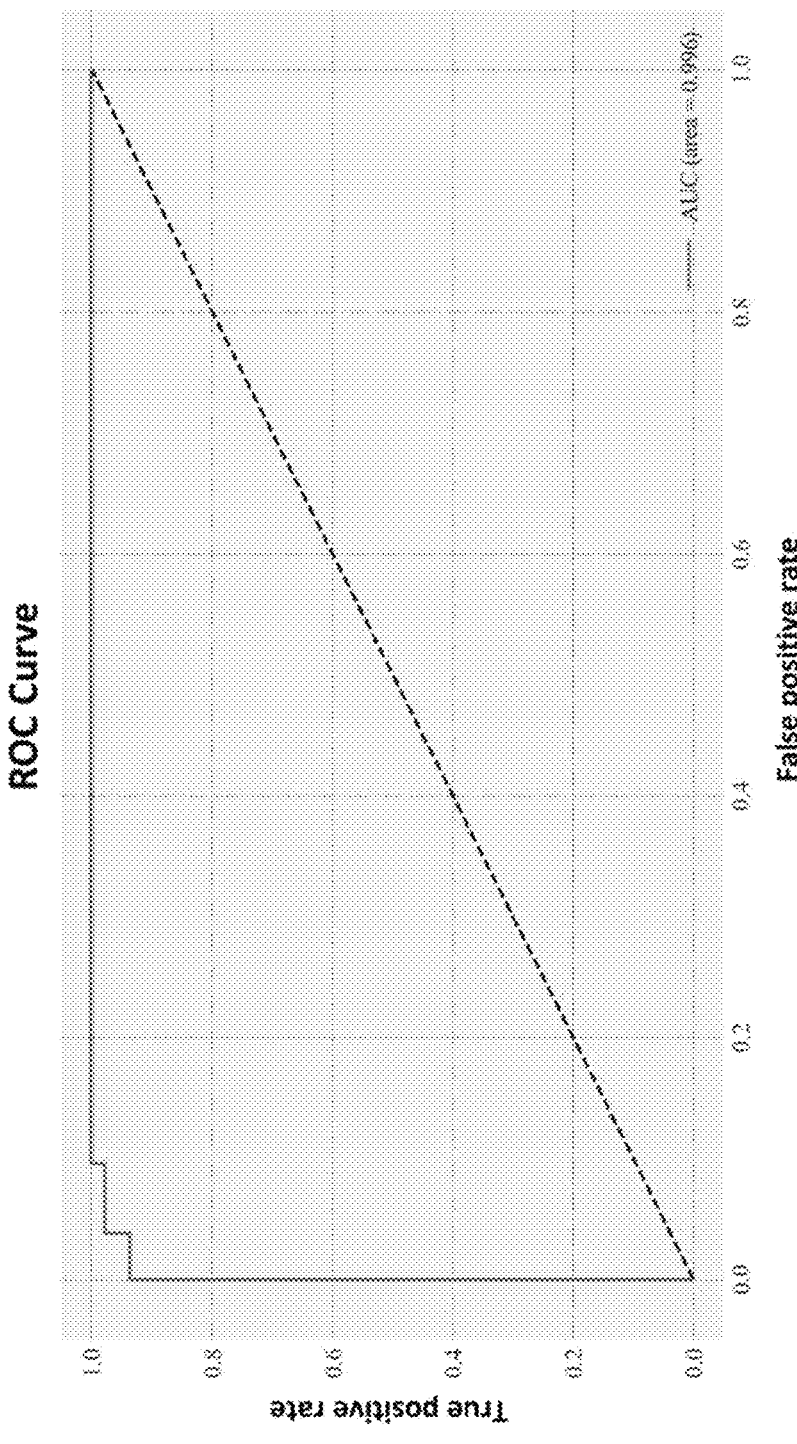
FIG. 15B shows a receiver-operating characteristic curve computed using the test set predicted stroke classifications, according to an embodiment.

FIG. 15B shows a receiver-operating characteristic curve computed using the test set predicted stroke classifications. The test set ROC curve is shown in FIG. 15B, demonstrating an AUC of 0.996 for the detection of stroke, suggesting that the classification DNN generalizes well using broadband S-parameter measurements as inputs.

Figure 16:
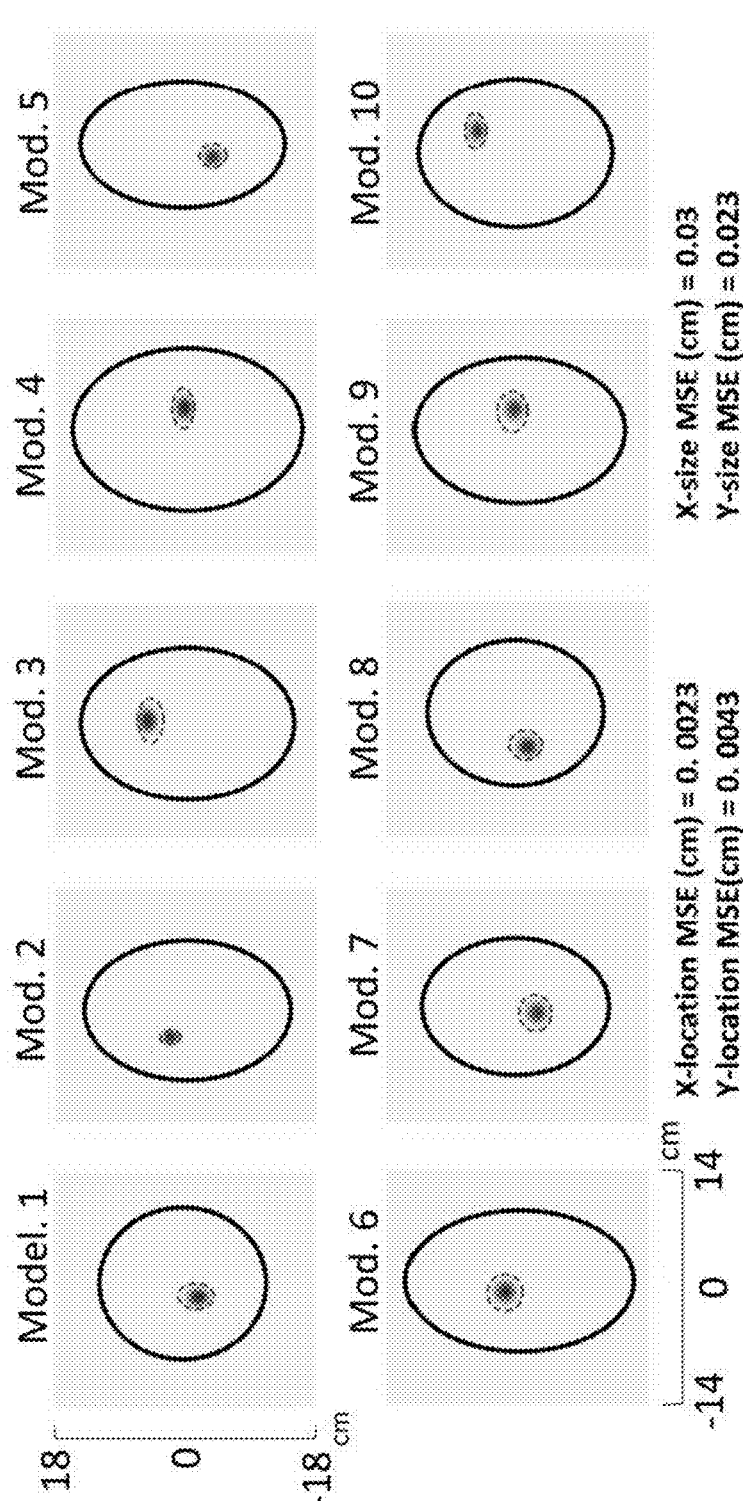
FIG. 16 shows a test set stroke predicted by the discrimination network, according to an embodiment.

FIG. 16 shows a test set stroke predicted by the discrimination network. True stroke size and location (dotted line) can be compared against the predicted strokes (Gaussians). Upon convergence of training, size and location of the strokes in 10 random head models from the test set cohort can be plotted in FIG. 16, where the dotted ovals represent the in silico stroke. As shown, varying head sizes as well as stroke locations and sizes can be used as inputs to the DNN. For clarity of representation, additional anatomic features (other than the stroke) were excluded. The predicted stroke size and location predicted by the DNN is illustrated as a 2D Gaussian probability density function shown. Test set MSE for stroke localization in the x- and y-directions was 0.0023 cm and 0.0043 cm, respectively, and stroke size MSE in the x- and y-directions was 0.03 cm and 0.023 cm, respectively.

Physical changes in tissue electrical properties (EPs) caused by hemorrhagic stroke can cause measurable changes in EM wave scattering. These changes in the S-parameter matrices can be used to train networks for intelligent diagnosis and discrimination of stroke. Broadband acquisitions between 0.5 and 6 GHz can provide complementary information. Multi-antenna and multi-frequency information shows that higher S-parameter disruptions at higher frequencies can occur due to the higher sensitivity in shallow depths, due to the skin effect, as well as the size of the lesion. These changes can provide information for the DNNs to facilitate learning the presence of stroke as well as the capability to localize and estimate the size of the stroke. The additional contrast arising from a broadband frequency sweep in a simulated cohort can be utilized to facilitate learning and generalization, while circumventing conventional MI reconstruction inverse problems.

Two-dimensional EM simulations can be employed due to computational demands inherent to three-dimensional simulations. More than 100,000 simulations can be conducted to calculate electromagnetic fields and thus S-parameters across all frequency, subject, and antenna permutations. The challenges inherent to engineering realistic, 3D patho-anatomic models for electromagnetic simulation can constitute ongoing motivation for the development of robust experimental methods. Reduction of the dimensionality to two-dimensions to alleviate computational demand can consequently eliminate the z-dimension (e.g., the craniocaudal direction) thus converting the hemorrhage to an affected 2D area of the simulated brain with Maxwell's equations solved in 2D. A transition to three dimensions in realizable antenna array systems could benefit from the utilization of a greater number of antennas, thus capturing 3D spatial detail such as that arising from a 3D hemorrhage volume within the head.

Improvements in the prediction of the presence, location, and size of intracranial hemorrhage can be achieved through machine learning-assisted MI by leveraging the additional contrast arising from broadband microwave frequencies. The machine learning device can output a predicted disease state based on one or more broadband microwave frequencies. The reduction in the number of frequency sweeps and/or coils used can result in acceleration of S-parameter acquisitions to improve patient comfort or time to diagnosis. Further, the selection of a simulated cohort of 666 stroke and control subjects constitutes only an initial approximation of an achievable cohort in contemporary stroke trials and is representative of stroke imaging workflow.

Acquisition systems capable of realizing this approach could employ wide-band antenna arrays encircling the patient's head. Each antenna can be connected to controllable RF/microwave switches routing each antenna to receive or transmit signals and connected to a multi-port vector network analyzer (VNA). Alternatively, SDRs can be utilized alongside directional couplers to gather wide-band scattering information. Such systems can be two orders of magnitude less expensive than state of the art imaging systems (e.g. clinical MRI).

Intracerebral hemorrhage was simulated. Blood can provide a stronger dielectric contrast than ischemia, which may be more pathologically variegated at the tissue level, challenging development of realistic simulated conditions. The detection accuracy for hemorrhage >1 cm in diameter (see Table 2 for stroke variation in x- and y-directions) was 94.6%, and therefore the dependable exclusion of hemorrhage can serve as a screening tool in the acute stroke setting to facilitate rapid thrombolysis as per current guidelines in early-presenting patients. This latter point bears emphasis, as intravenous thrombolysis remains the only approved pharmacologic therapy in acute ischemic stroke patients, but with rare exceptions cannot be administered beyond the initial, hyperacute window. Consequently, only 12% of patients receive critical intravenous thrombolysis, despite a 30% improvement in outcomes among those treated.

A method of detecting dielectric changes in matter can include obtaining microwave scattering data from a data collection array. The microwave scattering data can include at least one of incidence S-parameter data and scattering S-parameter data. The S-parameter data can include S-parameter matrices. The S-parameter matrices can include information of reflected and forward waves. The data collection array can include field programmable gate arrays, software defined radio, network analyzers, and other hardware.

The method can include receiving, by a machine learning device, the microwave scattering data, patient information, and imaging modality data corresponding to at least one of a presence of disease, absence of disease, or one or more disease features. The imaging modality data can include at least one of MR data, CT data, and PET data. The machine learning device can include a deep neural network machine learning device. The patient information can include at least one of patient medical history, age, dimensions of body, and sex.

The method can include analyzing, by the machine learning device, the microwave scattering data, patient information, and imaging modality data. The method can include outputting, by the machine learning device, at least one of a predicted disease state and predicted features based on the analyzed microwave scattering data, patient information, and imaging modality data. The at least one of the predicted disease state and predicted features can include a presence of hemorrhage.

The method can include comparing, by the machine learning device, the imaging modality data corresponding to the at least one of the presence of disease, absence of disease, or one or more disease features to at least one of the predicted disease state and predicted features. The method can include using, by the machine learning device, the comparison as an input into the machine learning device.

In some embodiments, the method can include using correlations between imaging modality data and microwave tomography to output the at least one of the predicted disease state and predicted features. In some embodiments, the machine learning device can output the at least one of the predicted disease state and predicted features based on one or more broadband microwave frequencies. In some embodiments, the machine learning device can include a classification network and a discrimination network. In some embodiments, the method can include outputting the at least one of the predicted disease state and predicted features based on one or more broadband microwave frequencies.

Systems and methods for hemorrhagic stroke detection and discrimination by means of learning disease dielectric signatures from S-parameter measurements using wide-band antenna arrays are described. Two DNN architectures were designed and tuned for classification and discrimination in presence of stroke in stochastic in silico, multi-compartment head models representing the tissue dielectric disturbances occurring in the setting of hemorrhagic stroke and derived from electromagnetic field simulations. The systems and methods of the present disclosure offer a potential strategy for rapid stroke detection and management, circumventing conventional image generation.

Figure 17:
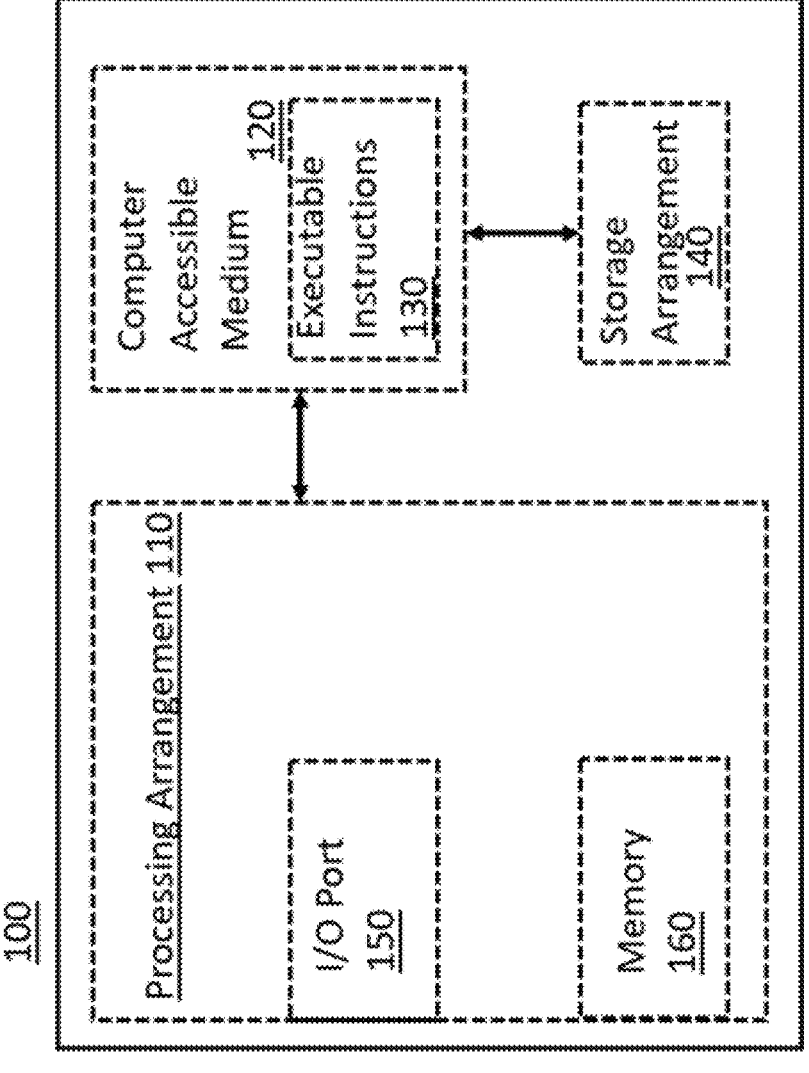
FIG. 17 illustrates a computer system for use with certain implementations.

As shown in FIG. 17, e.g., a computer-accessible medium 120 (e.g., as described herein, a storage device such as a hard disk, floppy disk, memory stick, CD-ROM, RAM, ROM, etc., or a collection thereof) can be provided (e.g., in communication with the processing arrangement 110). The computer-accessible medium 120 may be a non-transitory computer-accessible medium. The computer-accessible medium 120 can contain executable instructions 130 thereon. In addition, or alternatively, a storage arrangement 140 can be provided separately from the computer-accessible medium 120, which can provide the instructions to the processing arrangement 110 so as to configure the processing arrangement to execute certain exemplary procedures, processes and methods, as described herein, for example. The instructions may include a plurality of sets of instructions. For example, in some implementations, the instructions may include instructions for applying radio frequency energy in a plurality of sequence blocks to a volume, where each of the sequence blocks includes at least a first stage. The instructions may further include instructions for repeating the first stage successively until magnetization at a beginning of each of the sequence blocks is stable, instructions for concatenating a plurality of imaging segments, which correspond to the plurality of sequence blocks, into a single continuous imaging segment, and instructions for encoding at least one relaxation parameter into the single continuous imaging segment.

System 100 may also include a display or output device, an input device such as a key-board, mouse, touch screen or other input device, and may be connected to additional systems via a logical network. Many of the embodiments described herein may be practiced in a networked environment using logical connections to one or more remote computers having processors. Logical connections may include a local area network (LAN) and a wide area network (WAN) that are presented here by way of example and not limitation. Such networking environments are commonplace in office-wide or enterprise-wide computer networks, intranets and the Internet and may use a wide variety of different communication protocols. Those skilled in the art can appreciate that such network computing environments can typically encompass many types of computer system configurations, including personal computers, hand-held devices, multi-processor systems, microprocessor-based or programmable consumer electronics, network PCs, mini-computers, mainframe computers, and the like. Embodiments of the disclosure may also be practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

Various embodiments are described in the general context of method steps, which may be implemented in one embodiment by a program product including computer-executable instructions, such as program code, executed by computers in networked environments. Generally, program modules include routines, programs, objects, components, data structures, etc. that perform particular tasks or implement particular abstract data types. Computer-executable instructions, associated data structures, and program modules represent examples of program code for executing steps of the methods disclosed herein. The particular sequence of such executable instructions or associated data structures represents examples of corresponding acts for implementing the functions described in such steps.

Software and web implementations of the present invention could be accomplished with standard programming techniques with rule based logic and other logic to accomplish the various database searching steps, correlation steps, comparison steps and decision steps. It should also be noted that the words "component" and "module," as used herein and in the claims, are intended to encompass implementations using one or more lines of software code, and/or hardware implementations, and/or equipment for receiving manual inputs.

As used herein, the singular forms "a", "an" and "the" include plural referents unless the context clearly dictates otherwise. Thus, for example, the term "a member" is intended to mean a single member or a combination of members, "a material" is intended to mean one or more materials, or a combination thereof.

As used herein, the terms "about" and "approximately" generally mean plus or minus 10% of the stated value. For example, about 0.5 would include 0.45 and 0.55, about 10 would include 9 to 11, about 1000 would include 900 to 1100.

It should be noted that the term "exemplary" as used herein to describe various embodiments is intended to indicate that such embodiments are possible examples, representations, and/or illustrations of possible embodiments (and such term is not intended to connote that such embodiments are necessarily extraordinary or superlative examples).

The terms "coupled," "connected," and the like as used herein mean the joining of two members directly or indirectly to one another. Such joining may be stationary (e.g., permanent) or moveable (e.g., removable or releasable). Such joining may be achieved with the two members or the two members and any additional intermediate members being integrally formed as a single unitary body with one another or with the two members or the two members and any additional intermediate members being attached to one another.

It is important to note that the construction and arrangement of the various exemplary embodiments are illustrative only. Although only a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter described herein. Other substitutions, modifications, changes and omissions may also be made in the design, operating conditions and arrangement of the various exemplary embodiments without departing from the scope of the present invention.

While this specification contains many specific implementation details, these should not be construed as limitations on the scope of any inventions or of what may be claimed, but rather as descriptions of features specific to particular implementations of particular inventions. Certain features described in this specification in the context of separate implementations can also be implemented in combination in a single implementation. Conversely, various features described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

What is claimed is:

1. A system of reconstructing a dielectric image, comprising:
    a data collection array to collect microwave scattering data;
    a machine learning device configured to:
        receive the microwave scattering data;
        analyze the microwave scattering data;
        output a generated image based on the analyzed microwave scattering data;
        identify at least one of a presence of disease, absence of disease, or one or more disease features from the generated image.

2. The system of claim 1, wherein the machine learning device is trained and validated based on patient information and imaging modality data.

3. The system of claim 1, wherein the machine learning device is a deep neural network machine learning device.

4. The system of claim 1, wherein the data collection array comprises at least one of wide-band antenna, field programmable gate arrays, software defined radio, and network analyzers.

5. The system of claim 1, wherein the machine learning device is configured to select a reconstruction technique based on a population size.

6. The system of claim 1, wherein the system is integrated into a helmet.

7. The system of claim 1, wherein the machine learning device is configured to train a deep neural network classifier.

8. The system of claim 1, wherein the machine learning device is configured to output the at least one of a presence of disease, absence of disease, or one or more disease features.

9. The system of claim 1, wherein the machine learning device is configured to output the at least one of a presence of disease, absence of disease, or one or more disease features based on one or more broadband microwave frequencies.

10. The system of claim 1, wherein the machine learning device comprises a classification network and a discrimination network.

11. The system of claim 1, wherein the machine learning device is configured to receive imaging modality data corresponding to the at least one of a presence of disease, absence of disease, or one or more disease features.

12. The system of claim 1, wherein the machine learning device is configured to receive imaging modality data comprising at least one of MR data, CT data, or PET data.

13. The system of claim 1, wherein the machine learning device is configured to receive patient information comprising at least one of patient medical history, age, dimensions of body, or sex.

14. The system of claim 1, wherein the microwave scattering data comprises at least one of incidence S-parameter data or scattering S-parameter data.

15. The system of claim 1, wherein the machine learning device is configured to quantify temporal information of the one or more physiological attributes.

16. The system of claim 1, wherein the machine learning device is configured to output a diagnosis based on the analyzed microwave scattering data.

17. A method of reconstructing a dielectric image, comprising:
    obtaining microwave scattering data from a data collection array;
    receiving, by a machine learning device, the microwave scattering data;
    analyzing, by the machine learning device, the microwave scattering data;
    outputting, by the machine learning device, a generated image based on the analyzed microwave scattering data; and
    identifying, by the machine learning device, at least one of a presence of disease, absence of disease, one or more physiological attributes, or one or more disease features from the generated image.

18. The method of claim 17, wherein the machine learning device is configured to quantify temporal information of the one or more physiological attributes.

19. The method of claim 18, wherein the machine learning device is configured to output a diagnosis based on the analyzed microwave scattering data.

20. A non-transitory computer-accessible medium having stored thereon computer-executable instructions for reconstructing a dielectric image, wherein, when at least one computer processor executes the software, the computer processor is configured to perform the procedures, comprising:
    obtaining microwave scattering data from a data collection array;
    receiving, by a machine learning device, the microwave scattering data;
    analyzing, by the machine learning device, the microwave scattering data;
    outputting, by the machine learning device, a generated image based on the analyzed microwave scattering data; and
    identifying, by the machine learning device, at least one of a presence of disease, absence of disease, one or more physiological attributes, or one or more disease features from the generated image.

* * * * *